(12) United States Patent
Wang et al.

(10) Patent No.: US 7,625,555 B2
(45) Date of Patent: Dec. 1, 2009

(54) RECOMBINANT HUMAN INTERFERON-LIKE PROTEINS

(75) Inventors: Haitao Wang, Vancouver (CA); Chunsheng Mao, Vancouver (CA); Jizhi Li, Vancouver (CA); Jing Xu, Vancouver (CA); Rui Zhang, Vancouver (CA); Ling Wang, Vancouver (CA); Yong Du, Vancouver (CA); Longbin Liu, West Vancouver (CA)

(73) Assignee: Novagen Holding Corporation, George Town (KY)

( * ) Notice: Subject to any disclaimer, the term of this patent is extended or adjusted under 35 U.S.C. 154(b) by 0 days.

(21) Appl. No.: 11/764,786

(22) Filed: Jun. 18, 2007

(65) Prior Publication Data

US 2008/0312148 A1   Dec. 18, 2008

(51) Int. Cl.
*A61K 38/21* (2006.01)
*C07K 14/00* (2006.01)
*C08H 1/02* (2006.01)
*C12P 21/04* (2006.01)
*C07H 21/04* (2006.01)
*A61K 38/00* (2006.01)

(52) U.S. Cl. .................. 424/85.7; 435/69.51; 530/351; 530/402; 536/23.52; 514/12

(58) Field of Classification Search ................. None
See application file for complete search history.

(56) References Cited

U.S. PATENT DOCUMENTS

| | | | |
|---|---|---|---|
| 3,699,222 | A | 10/1972 | Isaacs et al. |
| 4,179,337 | A | 12/1979 | Davis et al. |
| 4,496,689 | A | 1/1985 | Mitra |
| 4,640,835 | A | 2/1987 | Shimizu et al. |
| 4,791,192 | A | 12/1988 | Nakagawa et al. |
| 4,885,166 | A | 12/1989 | Meyer et al. |
| 4,914,033 | A | 4/1990 | Bell et al. |
| 5,055,289 | A | 10/1991 | Frincke et al. |
| 5,071,761 | A | 12/1991 | Meyer et al. |
| 5,137,720 | A | 8/1992 | Gangemi et al. |
| 5,605,793 | A | 2/1997 | Stemmer |
| 5,681,811 | A | 10/1997 | Ekwuribe |
| 5,711,944 | A | 1/1998 | Gilbert et al. |
| 5,738,846 | A | 4/1998 | Greenwald et al. |
| 5,908,626 | A | 6/1999 | Chang et al. |
| 6,174,708 | B1 | 1/2001 | Sodoyer et al. |
| 6,174,996 | B1 | 1/2001 | Johnson et al. |
| 6,514,729 | B1 | 2/2003 | Bentzien |
| 6,531,122 | B1 | 3/2003 | Pedersen et al. |
| 6,569,420 | B2 | 5/2003 | Chen et al. |
| 6,685,933 | B1 | 2/2004 | Zoon et al. |
| 6,946,296 | B2 | 9/2005 | Patten et al. |
| 7,498,152 | B1 | 3/2009 | Patten et al. |
| 2003/0175241 | A1 | 9/2003 | Pedersen et al. |
| 2004/0002474 | A1 | 1/2004 | Heinrichs et al. |
| 2004/0013644 | A1 | 1/2004 | Rasmussen et al. |
| 2004/0203118 | A1 | 10/2004 | Escary |
| 2005/0201982 | A1 | 9/2005 | Hazel et al. |
| 2005/0249703 | A1 | 11/2005 | Jensen |
| 2006/0051859 | A1 | 3/2006 | Fu et al. |
| 2007/0025966 | A1 | 2/2007 | Patten et al. |
| 2007/0254838 | A1 | 11/2007 | Gantier et al. |

FOREIGN PATENT DOCUMENTS

| | | |
|---|---|---|
| CN | 1431018 A | 7/2003 |
| WO | 0115736 A2 | 3/2001 |
| WO | 0125438 A2 | 4/2001 |
| WO | 0136001 A2 | 5/2001 |
| WO | 0172993 A1 | 10/2001 |
| WO | 0236627 A2 | 5/2002 |
| WO | 0236628 A2 | 5/2002 |
| WO | 02074806 A2 | 9/2002 |
| WO | 02081507 A2 | 10/2002 |
| WO | 03002152 A2 | 1/2003 |
| WO | 03075944 A2 | 9/2003 |
| WO | 2004005341 A2 | 1/2004 |
| WO | 2004020468 A2 | 3/2004 |
| WO | 2004046365 A2 | 6/2004 |
| WO | 2005113592 A2 | 12/2005 |

OTHER PUBLICATIONS

Pr001305760, NCBI Probe DB (Applied Biosystems), Oct. 5, 2005, see 1305760c.1 RSA primer.
Interferon nomenclature. Nature. 1980; 286 (5769):110.
Jonasch E and Haluska FG. Interferon in oncological practice: review of interferon biology, clinical applications, and toxicities. Oncologist. 2001; 6(1):34-55.
Lengyel P. Biochemistry of interferons and their actions. Annu Rev Biochem. 1982; 51:251-282.
Gresser I and Tovey MG. Antitumor effects of interferon. Biochim Biophys Acta. 1978; 516(2):231-247.
Samuel CE. Antiviral actions of interferons. Clin Microbiol Rev. 2001;14(4):778-809.

(Continued)

*Primary Examiner*—Christine J Saoud
*Assistant Examiner*—Elly-Gerald Stoica
(74) *Attorney, Agent, or Firm*—Oyen Wiggs Green & Mutala LLP

(57) ABSTRACT

This application relates to recombinant human interferon-like proteins. In one embodiment a recombinant protein created by gene shuffling technology is described having enhanced anti-viral and anti-proliferative activities in comparison to naturally occurring human interferon alpha 2b (HuIFN-α2b). The invention encompasses a polynucleotide encoding the protein and recombinant vectors and host cells comprising the polynucleotide. Preferably the polynucleotide is selected from the group of polynucleotides each having a sequence at least 93% identical to SEQ ID: No. 1 and the protein is selected from the group of proteins each having an amino acid sequence at least 85% identical to SEQ ID No: 2. The proteins and compositions comprising the proteins can be used for treatment of conditions responsive to interferon therapy, such as viral diseases and cancer.

34 Claims, 9 Drawing Sheets

OTHER PUBLICATIONS

Theofilopoulos AN, et al. Type I interferons (alpha/beta) in immunity and autoimmunity. Annu Rev Immunol. 2005; 23:307-336.

Uze G, et al. Alpha and beta interferons and their receptor and their friends and relations. J Interferon Cytokine Res. 1995; 15(1): 3-26.

Knight E Jr. Interferon: purification and initial characterization from human diploid cells. Proc Natl Acad Sci USA. 1976; 73(2):520-523.

Pestka S, et al. Interferons, interferon-like cytokines, and their receptors. Immunol Rev. 2004; 202:8-32.

Horisberger MA and Di Marco S. Interferon-alpha hybrids. Pharmacol Ther. 1995; 66(3):507-534.

Horton HM, et al. Antitumor effects of interferon-omega: in vivo therapy of human tumor xenografts in nude mice. Cancer Res. 1999; 59(16):4064-4068.

Hardy MP, et al. Characterization of the type I interferon locus and identification of novel genes. Genomics.2004; 84 (2):331-345.

Pestka S, et al. Interleukin-10 and releated cytokines and receptors. Annu Rev Immunol 2004, 22:929-979.

Nardelli B, et al. Regulatory effect of IFN-kappa, a novel type I IFN, on cytokine production by cells of the innate immune system. J. Immunol. 2002; 169(9):4822-4830.

LaFleur DW, et al. Interferon-kappa, a novel type I interferon expressed in human keratinocytes. J Biol Chem. 2001; 276(43): 39765-39771.

Subramaniam PS, Johnson HM. The IFNAR1 subunit of the type I IFN receptor complex contains a functional nuclear localization sequence. FEBS Lett. 2004; 578(3):207-210.

Goodbourn S, et al. Interferons: cell signalling, immune modulation, antiviral response and virus countermeasures. J Gen Virol. 2000; 81(Pt 10):2341-2364.

Wang K, et al. Inhibition of neutrophil apoptosis by type 1 IFN depends on cross-talk between phosphoinositol 3-kinase, protein kinase C-delta, and NF-kappa B signaling pathways. J Immunol. 2003; 171(2):1035-1041.

Katze MG. Interferon, PKR, virology, and genomics: what is past and what is next in the new millennium? J Interferon Cytokine Res. 2002; 22(3):283-286.

Chawla-Sarkar M, et al. Apoptosis and interferons: role of interferon-stimulated genes as mediators of apoptosis. Apoptosis. 2003; 8(3):237-249.

Kirkwood J. Cancer immunotherapy: the interferon-alpha experience. Semin Oncol. 2002; 29(3 Suppl 7):18-26.

Hofmann V, et al. Hairy cell leukemia: an interferon deficient disease? Cancer Treat Rev. 1985; Suppl B: 33-37.

Stone RM , et al. Recombinant human gamma interferon administered by continuous intravenous infusion in acute myelogenous leukemia and myelodysplastic syndromes. Am J Clin Oncol. 1993; 16(2):159-163.

Talpaz M, et al. Human leukocyte interferon to control thrombocytosis in chronic myelogenous leukemia. Ann Intern Med. 1983; 99(6):789-792.

Talpaz M, et al. Changes in granulocyte-monocyte colony-forming cells among leukocyte-interferon-treated chronic myelogenous leukemia patients. Exp Hematol. 1986; 14(7):668-671.

Strander H, et al. Long-term adjuvant interferon treatment of human osteosarcoma. A pilot study. Acta Oncol. 1995; 34(6):877-880.

Dogan B, et al. Intralesional alfa-2a interferon therapy for basal cell carcinoma. Cancer Lett. 1995; 91(2):215-219.

Fetell MR, et al. Intratumor administration of beta-interferon in recurrent malignant gliomas. A phase I clinical and laboratory study. Cancer. 1990; 65(1):78-83.

Muss HB. The use of interferon in renal cell carcinoma. Eur J Cancer. 1991; 27 (Suppl 4):S84-87.

Peest D, et al. Cytokine therapy in multiple myeloma. Br. J Haematol. 1996; 94(3):425-432.

Ikic D, et al. Local interferon therapy for melanoma patients. Int. J Dermatol. 1995; 34(12):872-874.

Rybak ME, et al. Interferon therapy of relapsed and refractory Hodgkin's disease: Cancer and Leukemia Group B Study 8652. J Biol. Response Mod. 1990; 9(1):1-4.

Kaufmann R, et al. Temozolomide in combination with interferon-alpha versus temozolomide alone in patients with advanced metastatic melanoma: a randomized, phase III, multicenter study from the Dermatologic Cooperative Oncology Group. J Clin Oncol. 2005; 23(35):9001-9007.

Lane HC. The role of alpha-interferon in patients with human immunodeficiency virus infection. Semin Oncol. 1991; 18(Suppl 7):46-52.

Woo MH and Brunakis TG. Interferon alfa in the treatment of chronic viral hepatitis B and C. Ann. Pharmacother. 1997; 31(3):330-337.

Gibas AL. Use of interferon in the treatment of chronic viral hepatitis. Gastroenterologist. 1993; 1(2):129-142.

Levine LA, et al. Treatment of subclinical intraurethral human papilloma virus infection with interferon alfa-2b. Urology. 1996; 47(4):553-557.

Ho M. Interferon for the treatment of infections. Annu Rev Med. 1987; 38:51-59.

Wintergerst U and Belohradsky BH. Acyclovir monotherapy versus acyclovir plus beta-interferon in focal viral encephalitis in children. Infection. 1992; 20(4):207-212.

Bogdan C, et al. The role of type I interferons in non-viral infections. Immunol Rev. 2004; 202:33-48.

Condos R, et al. Treatment of multidrug-resistant pulmonary tuberculosis with interferon-gamma via aerosol. Lancet. 1997; 349(9064):1513-1514.

Giosue S, et al. Aerosolized interferon-alpha treatment in patients with multi-drug-resistant pulmonary tuberculosis. Eur Cytokine Netw. 2000; 11(1):99-104.

Raad I, et al. Use of adjunctive treatment with interferon-gamma in an immunocompromised patient who had refractory multidrug-resistant tuberculosis of the brain. Clin Infect Dis. 1996; 22:572-574.

Fernandez O, et al. Treatment of relapsing-remitting multiple sclerosis with natural interferon beta: a multicenter, randomized clinical trial. Mult. Scler. 1995; Suppl 1:S67-69.

Freedman MS, et al. Randomized study of once-weekly interferon beta-Ia therapy in relapsing multiple sclerosis: three-year data from the OWIMS study. Mult Scler. 2005; 11(1):41-45.

Shiozawa S, et al. Single-blinded controlled trial of low-dose oral IFN-alpha for the treatment of xerostomia in patients with Sjogren's syndrome. J Interferon Cytokine Res. 1998; 18(4):255-262.

Wandinger KP, et al. Diminished production of type-I interferons and interleukin-2 in patients with multiple sclerosis. J Neurol Sci. 1997; 149(1):87-93.

Steegmann JL, et al. Interferon alpha for chronic myeloid leukemia relapsing after allogeneic bone marrow transplantation. Bone Marrow Transplant. 1999; 23(5):483-488.

Kirkwood JM, et al. High dose Interferon alfa 2b significantly prolongs relapse free survival compared with GM2-KLH/QS-21 vaccine in patients with resected stage IIB-III melanoma: Results of Intergroup Trial E1694/S9512/C509081. J Clin Oncol 2001; 19:2370-2380.

Bonnem EM. alpha Interferon: the potential drug of adjuvant therapy: past achievements and future challenges. Eur J Cancer. 1991; 27 Suppl 4:S2-6.

Folkman J. Successful treatment of an angiogenic disease. N. Engl J Med. 1989; 320:1211-1212.

Clifford JL, et al. Retinoids and interferons as antiangiogenic cancer drugs. In: Teicher BA, ed. Antiangiogenic Agents in Cancer Therapy. Totowa, NJ: Humana Press Inc; 1999; 355-370.

Kaban LB, et al. Antiangiogenic therapy of a recurrent giant cell tumor of the mandible with interferon alfa-2a. Pediatrics. 1999; 103:1145-1149.

Sleijfer S, et al. Side effects of interferon-alpha therapy. Pharm World Sci. 2005; 27(6):423-431.

Streuli M, et al. Target cell specificity of two species derived from them. Proc Natl Acad Sci USA. 1981; 78(5): 2848-2852.

Raj, NB, et al. Synthesis, antiviral activity, and conformational characterization of mouse-human a-interferon hybrids. J Biol Chem. 1988; 263(18):8943-8952.

Mark DF, et al. Site-specific mutagenesis of the human fibroblast interferon gene. Proc Natl Acad Sci USA 1984; 81 (18): 5662-5666.

Chang CC, et al. Evolution of a cytokine using DNA family shuffling. Nat Biotechnol. 1999; 17(8):793-797.

Blatt LM, et al. The biologic activity and molecular characterization of a novel synthetic interferon-alpha species, consensus interferon. J interferon cytokine Res. 1996; 16:489-499.

Bowie JU, et al. Deciphering the Message in Protein Sequences: Tolerance to Amino acid Substitutions. Science 1990; 247(4948):1306-1310.

Creighton TE. Posttranslational covalent modification of polypeptide chains. In Proteins: Structure and Molecular Properties. Ed by Creighton TE. W. H. Freeman & Co. 1993; pp. 78-99. San Francisco, US.

Aplin JD and Wriston JC Jr. Preparation, properties, and applications of carbohydrate conjugates of proteins and lipids. CRC Crit Rev Biochem. 1981; 10(4):259-306.

Edge AS, et al. Deglycosylation of glycoproteins by trifluoromethanesulfonic acid. Anal Biochem. 1981; 118 (1):131-137.

Thotakura NP and Bohl OP. Enzymatic deglycosylation of glycoproteins. Meth Enzymol.1987; 138:350-359.

Field J, et al. Purification of a RAS-responsive adenylyl cyclase complex from *Saccharomyces cerevisiae* by use of an epitope addition method. Mol Cell Biol. 1988; 8(5):2159-2165.

Evan GI, et al. Isolation of monoclonal antibodies specific for human c-myc proto-oncogene product. Mol Cell Biol. 1985; 5(12):3610-3616.

Paborsky LR, et al. Mammalian cell transient expression of tissue factor for the production of antigen. Protein Eng. 1990; 3(6):547-553.

Einhauer A and Jungbauer A. The FLAG peptide, a versatile fusion tag for the purification of recombinant proteins. J Biochem Biophys Methods. 2001; 49(1-3):455-465.

Skinner H, et al. Use of the Glu-Glu-Phe C-terminal epitope for rapid purification of the catalytic domain of normal and mutant ras GTPase-activating proteins. J Biol Chem. 1991; 266(22):14163-14166.

Lutz-Freyermuth C, et al. Quantitative determination that one of two potential RNA-binding domains of the A protein component of the U1 small nuclear ribonucleoprotein complex binds with high affinity to stem-loop II of U1 RNA. Proc Natl Acad Sci USA. 1990; 87(16):6393-6397.

Zhang ZQ, et al. Construction and application of a high level expression vector containing PRPL promoter. Chinese J of Virol. 1990; 2:18-23.

McNeill TA. Interferon assay. J Immunol Methods. 1981; 46(2):121-127.

Rubinstein S, et al. Convenient assay for interferons. J. Virol. 1981; 37: 755-758.

Horisberger MA and de Staritzky K. A recombinant human interferon-α B/D hybrid with a broad host-range. J Gen Virol. 1987; 68:945-948.

Stitz L and Schellekens H. Influence of input multiplicity of infection on the antiviral activity of interferon. J Gen Virol. 1980; 46:205-210.

Yeo EY, et al. Effect of short-term ethanol on the proliferative response of Swiss 3T3 cells to mitogenic growth factors, Exp Mol Med. 2000: 32:161-169.

Vignesh RC, et al. Effect of ethanol on human osteosarcoma cell proliferation, differentiation and mineralization. Toxicology. 2006; 220(1):63-70.

Cavanaugh PF Jr, et al. A semi-automated neutral red based chemosensitivity assay for drug screening. Investigational New Drugs. 1990; 8(4):347-354.

Raines EW and Ross R. Purification of human platelet-derived growth factor. Methods Enzymol. 1985; 109:749-773.

Wahl AF, et al. Gene expression of human DNA polymerase alpha during cell proliferation and the cell cycle. Mol Cell Biol. 1988; 8(11):5016-5025.

Cook JA and Mitchel JB. Viability measurements in mammalian cell systems. Anal Biochem. 1989; 179(1):1-7.

Porstmann T, et al. Quantitation of 5-bromo-2-deoxyuridine incorporation into DNA: an enzyme immunoassay for the assessment of the lymphoid cell proliferative response. J Immunol Methods. 1985; 82(1):169-179.

Mosmann T. Rapid colorimetric assay for cellular growth and survival: application to proliferation and cytotoxicity assays. J Immunol Methods. 1983; 65(1-2):55-63.

Scudiero DA, et al. Evaluation of a soluble tetrazolium/formazan assay for cell growth and drug sensitivity in culture using human and other tumor cell lines. Cancer Res. 1988; 48(17):4827-4833.

Evinger M and Pestka S. Assay of growth inhibition in lymphoblastoid cell cultures. Methods Enzymol. 1981; 79(Pt B):362-368.

Meister A, et al. Biological activities and receptor binding of two human recombinant interferons and their hybrids. J Gen Virol. 1986; 67(Pt 8):1633-43.

Nieforth KA, et al. Use of an indirect pharmacodynamic stimulation model of MX protein induction to compare in vivo activity of interferon alfa-2a and a polyethylene glycol-modified derivative in healthy subjects. Clin Pharmacol Ther. 1996; 59(6):636-646.

Letsinger RL, et al. Cholesteryl-conjugated oligonucleotides: synthesis, properties, and activity as inhibitors of replication of human immunodeficiency virus in cell culture. Proc. Natl Acad Sci USA. 1989; 86(17): 6553-6556.

Brower V. Naked DNA vaccines come of age. Nat Biotechnol. 1998; 16(13):1304-1305.

Stemmer WP. DNA shuffling by random fragmentation and reassembly: in vitro recombination for molecular evolution. Proc Natl Acad Sci USA. 1994; 91(22): 10747-10751.

Armstrong JA. Cytopathic effect inhibition assay for interferon: microculture plate assay. Methods Enzymol. 1981; 78(pt A): 381-387.

Chou TC, et al. Reversal of anticancer multidrug resistance by the ardeemins. Proc Natl Acad Sci USA. 1998; 95(14):8369-8374.

Corbell T, et al. in vivo methods for screening and preclinical testing: use of rodent solid tumors for drug discovery. in Anticancer Drug Development Guide: preclinical screening, clinical trails, and approval. Edited by Teicher BA and Andrews PA. 2004; p. 79-124. Humana Press, New Jersey, US.

Brideau-Andersen, Amy D. et al., Directed Evolution of Gene-shuffled IFN—Molecules With Activity Profiles Tailored for Treatment of Chronic Viral Diseases, PNAS, vol. 104, No. 20, 2007, 8269-8274, May 15, 2007.

A

SEQ ID NO:1
TGTAATCTGTCTCAAACCCACAGCCTGGGTAGCAAGAGGACCTTGATGCTCCTGGCGCAGATGGGGAAAATC
TCCCTTTTCTCCTGCCTGAAGGACAGACATGACTTTGAATTTCCCCAGGAGGAATTTGATGGCAACCAGTTC
CAGAAAGCTCAAGCCATCTCTGTCCTCCATGAGCTGATCCAGCAGACCTTCAATCTCTTCAGCACAAAGGAA
TCATCTGCTGCTTGGGATGAGGGCCTCCTAGACAAATTCCGCACCGAACTCTACCGGCAGCTAAATGACTTG
GAAGCCTGTATGATGCAGGAGGTTGGGGTGGAAGAGACTCCCCTGATGAATGCGGACTCCATCCTGGCTGTG
AAGAAATACTTCCAAAGAATCACTCTTTATCTGATGGAGAAGAAATACAGCCCTTGTGCCTGGGAGGTTGTC
AGAGTAGAAATCATGAGATCCCTCTCTTTTTCAACAAACTTGCAAAAAGATTAAGGGGGAAGGAT

B

SEQ ID NO:2
CNLSQTHSLGSKRTLMLLAQMGKISLFSCLKDRHDFEFPQEEFDGNQFQKA
QAISVLHELIQQTFNLFSTKESSAAWDEGLLDKFRTELYRQLNDLEACMMQ
EVGVEETPLMNADSILAVKKYFQRITLYLMEKKYSPCAWEVVRVEIMRSLS
FSTNLQKRLRGKD

C

```
DNA      1   TGTAATCTGTCTCAAACCCACAGCCTGGGTAGCAAGAGGACCTTGATGCTC
Protein  1   C  N  L  S  Q  T  H  S  L  G  S  K  R  T  L  M  L DNA      52  CTGGCGCAGATGGGGAAAATCTCCCTTTTCTCCTGCCTGAAGGACAGACAT
Protein  18  L  A  Q  M  G  K  I  S  L  F  S  C  L  K  D  R  H DNA      103 GACTTTGAATTTCCCCAGGAGGAATTTGATGGCAACCAGTTCCAGAAAGCT
Protein  35  D  F  E  F  P  Q  E  E  F  D  G  N  Q  F  Q  K  A DNA      154 CAAGCCATCTCTGTCCTCCATGAGCTGATCCAGCAGACCTTCAATCTCTTC
Protein  52  Q  A  I  S  V  L  H  E  L  I  Q  Q  T  F  N  L  F DNA      205 AGCACAAAGGAATCATCTGCTGCTTGGGATGAGGGCCTCCTAGACAAATTC
Protein  69  S  T  K  E  S  S  A  A  W  D  E  G  L  L  D  K  F DNA      256 CGCACCGAACTCTACCGGCAGCTAAATGACTTGGAAGCCTGTATGATGCAG
Protein  86  R  T  E  L  Y  R  Q  L  N  D  L  E  A  C  M  M  Q DNA      307 GAGGTTGGGGTGGAAGAGACTCCCCTGATGAATGCGGACTCCATCCTGGCT
Protein  103 E  V  G  V  E  E  T  P  L  M  N  A  D  S  I  L  A DNA      358 GTGAAGAAATACTTCCAAAGAATCACTCTTTATCTGATGGAGAAGAAATAC
Protein  120 V  K  K  Y  F  Q  R  I  T  L  Y  L  M  E  K  K  Y DNA      409 AGCCCTTGTGCCTGGGAGGTTGTCAGAGTAGAAATCATGAGATCCCTCTCT
Protein  137 S  P  C  A  W  E  V  V  R  V  E  I  M  R  S  L  S DNA      460 TTTTCAACAAACTTGCAAAAAGATTAAGGGGGAAGGAT
protein  154 F  S  T  N  L  Q  K  R  L  R  G  K  D
```

```
Novaferon     1 TGTAATCTGTCTCAAACCCACAGCCTGGGTAGCAAGAGGACCTTGATGCTCCTGGCGCAG
                ||||||||||||||||||||||||||||| || || ||||||| |||||||| |||| ||
IFNα14      126 TGTAATCTGTCTCAAACCCACAGCCTGAATAACAGGAGGACTTTGATGCTCATGGCACAA Novaferon    61 ATGGGGAAAATCTCCCTTTTCTCCTGCCTGAAGGACAGACATGACTTTGAATTTCCCCAG
                ||| ||| |||||| | |||||||||||||||||||||||||||||||||||||||||||
IFNα14      186 ATGAGGAGAATCTCTCCTTTCTCCTGCCTGAAGGACAGACATGACTTTGAATTTCCCCAG Novaferon   121 GAGGAATTTGATGGCAACCAGTTCCAGAAAGCTCAAGCCATCTCTGTCCTCCATGAGCTG
                |||||||||||||||||||||||||||||||||||||||||||||||||||||||||| |
IFNα14      246 GAGGAATTTGATGGCAACCAGTTCCAGAAAGCTCAAGCCATCTCTGTCCTCCATGAGATG Novaferon   181 ATCCAGCAGACCTTCAATCTCTTCAGCACAAAGGAATCATCTGCTGCTTGGGATGAGGGC
                || ||||||||||||||||||||||||||||| | ||||||||||||||||||||||| |
IFNA14      306 ATGCAGCAGACCTTCAATCTCTTCAGCACAAAGAACTCATCTGCTGCTTGGGATGAGACC Novaferon   341 CTCCTAGACAAATTCCGCACCGAACTCTACCGGCAGCTAAATGACTTGGAAGCCTGTATG
                ||||||| ||||| || || ||||| | || ||| | ||||||| |||||||||||| ||
IFNα14      366 CTCCTAGAAAAATTCTACATTGAACTTTTCCAGCAAATGAATGACCTGGAAGCCTGTGTG Novaferon   301 ATGCAGGAGGTTGGGGTGGAAGAGACTCCCCTGATGAATGCGGACTCCATCCTGGCTGTG
                || ||||||||||||||||||||||||||||||||||||| |||||||||||||||||||
IFNα14      426 ATACAGGAGGTTGGGGTGGAAGAGACTCCCCTGATGAATGAGGACTCCATCCTGGCTGTG Novaferon   361 AAGAAATACTTCCAAAGAATCACTCTTTATCTGATGGAGAAGAAATACAGCCCTTGTGCC
                ||||||||||||||||||||||||||||||||||||||||||||||||||||||||||||
IFNα14      486 AAGAAATACTTCCAAAGAATCACTCTTTATCTGATGGAGAAGAAATACAGCCCTTGTGCC Novaferon   421 TGGGAGGTTGTCAGAGTAGAAATCATGAGATCCCTCTCTTTTTCAACAAACTTGCAAAAA
                ||||||||||||||||| |||||||||||||||| |||||||||||||||||||||||||
IFNα14      546 TGGGAGGTTGTCAGAGCAGAAATCATGAGATCCTTCTCTTTTTCAACAAACTTGCAAAAA Novaferon   481 AGATTAAGGGGGAAGGAT 498
                ||||||||| ||||||||
IFNα14      606 AGATTAAGGAGGAAGGAT 623
```

B

```
Novaferon     1  CNLSQTHSLGSKRTLMLLAQMGKISLFSCLKDRHDFEFPQEEFDGNQFQK
IFNα14       24  .........NNR.....M...RR..P........................

Novaferon    51  AQAISVLHELIQQTFNLFSTKESSAAWDEGLLDKFRTELYRQLNDLEACM
IFNα14       73  ..........MM..........N.......T..E..YI..FQ.M.....V Novaferon   101  MQEVGVEETPLMNADSILAVKKYFQRITLYLMEKKYSPCAWEVVRVEIMR
IFNα14      123  I............E...............................A....

Novaferon   151  SLSFSTNLQKRLRGKD 166
IFNα14      173  .............R.. 189
```

```
Novaferon    1 TGTAATCTGTCTCAAACCCACAGCCTGGGTAGCAAGAGGACCTTGATGCTCCTGGCGCAG
               ||| ||||| |||||||||||||||||||||||| |||||||||||||||||||||| |||
IFNα2b     138 TGTGATCTGCCTCAAACCCACAGCCTGGGTAGCAGGAGGACCTTGATGCTCCTGGCACAG Novaferon   61 ATGGGGAAAATCTCCCTTTTCTCCTGCCTGAAGGACAGACATGACTTTGAATTTCCCCAG
               ||| ||| |||||| ||||||||||||||||||||||||||||||||||| |||||||||
IFNα2b     198 ATGAGGAGAATCTCTCTTTTCTCCTGCTTGAAGGACAGACATGACTTTGGATTTCCCCAG Novaferon  121 GAGGAATTTGATGGCAACCAGTTCCAGAAAGCTCAAGCCATCTCTGTCCTCCATGAGCTG
               ||||| ||||   |||||||||||||| || ||| || ||||| |||||||||||| ||
IFNα2b     258 GAGGAGTTTG---GCAACCAGTTCCAAAAGGCTGAAACCATCCCTGTCCTCCATGAGATG Novaferon  181 ATCCAGCAGACCTTCAATCTCTTCAGCACAAAGGAATCATCTGCTGCTTGGGATGAGGGC
               |||||||||| ||||||||||||||||||||||| |||||||||||||||||||||| |
IFNα2b     315 ATCCAGCAGATCTTCAATCTCTTCAGCACAAAGGACTCATCTGCTGCTTGGGATGAGACC Novaferon  241 CTCCTAGACAAATTCCGCACCGAACTCTACCGGCAGCTAAATGACTTGGAAGCCTGTATG
               |||||||||||||| ||| |||||||||||| |||||| |||||| ||||||||||| ||
IFNα2b     375 CTCCTAGACAAATTCTACACTGAACTCTACCAGCAGCTGAATGACCTGGAAGCCTGTGTG Novaferon  301 ATGCAGGAGGTTGGGGTGGAAGAGACTCCCCTGATGAATGCGGACTCCATCCTGGCTGTG
               || ||||| ||| |||||||||||||||||||| ||| ||||||||||||||||||||||
IFNα2b     435 ATACAGGGGGTGGGGGTGACAGAGACTCCCCTGATGAAGGAGGACTCCATTCTGGCTGTG Novaferon  361 AAGAAATACTTCCAAAGAATCACTCTTTATCTGATGGAGAAGAAATACAGCCCTTGTGCC
               | |||||||||||||||||||||||| ||||||| ||||||||||||||||||||||||
IFNα2b     495 AGGAAATACTTCCAAAGAATCACTCTCTATCTGAAAGAGAAGAAATACAGCCCTTGTGCC Novaferon  421 TGGGAGGTTGTCAGAGTAGAAATCATGAGATCCCTCTCTTTTTCAACAAACTTGCAAAAA
               ||||||||||||||| |||||||||||||| |||| | ||||| |||||||||||| ||
IFNα2b     555 TGGGAGGTTGTCAGAGCAGAAATCATGAGATCTTTTCTTTGTCAACAAACTTGCAAGAA Novaferon  481 AGATTAAGGGGGAAGGAT 498
               || |||||  | |||||
IFNα2b     615 AGTTTAAGAAGTAAGGAA 632
```

B

```
Novaferon    1   CNLSQTHSLGSKRTLMLLAQMGKISLFSCLKDRHDFEFPQEEFDGNQFQK
IFNα2b       1   .D.P......R.........RR..............F...........

Novaferon   50   AQAISVLHELIQQTFNLFSTKESSAAWDEGLLDKFRTELYRQLNDLEACM
IFNα2       49   .ET.....E...Q.......K.......E.....F....Y........CV Novaferon  100   MQEVGVEETPLMNADSILAVKKYFQRITLYLMEKKYSPCAWEVVRVEIMR
IFNα2b      99   I.G...T.....KE......R..........K.............A....

Novaferon  150   SLSFSTNLQKRLRGKD 166
IFNα2b     149   .F.L.....ES..S.E 165
```

FIG. 3

RECOMBINANT HUMAN INTERFERON-LIKE PROTEINS

FIELD OF THE INVENTION

This application relates to recombinant proteins having human interferon-like biological activities.

BACKGROUND

In this application the interferon (IFN) nomenclature published in *Nature* (1) has been adopted.

Human interferons (HuIFNs), which were discovered by Isaacs and Lindenmann in 1957 (2), are a well-known family of cytokines secreted by a large variety of eukaryotic cells upon exposure to various stimuli, such as viral infection or mitogen exposure. IFNs can elicit many changes in cellular behavior, including effects on cellular growth and differentiation and modulation of the immune system (3-7). HuIFNs have been classified into six subgroups, namely IFN-α, IFN-β, IFN-γ. IFN-ω, IFN-ε and IFN-κ. HuIFN-α (leukocyte-derived interferon) is produced in human leukocyte cells and, together with minor amounts of HuIFN-β (fibroblast-derived interferon), in lymphoblastoid cells. HuIFNs have been further classified by their chemical and biological characteristics into two general categories, namely Type I and Type II. Type I consists of the IFN-α and INF-β subgroups as well as the recently discovered IFN-ω, IFN-ε and IFN-κ subgroups. Type II has only has one member: IFN-γ (immune interferon).

The different interferon subgroups have different structural and biological characteristics. HuIFN-β is an N-linked glycoprotein (8, 9) which has been purified to homogeneity and characterized. It is heterogeneous in regard to size, presumably due to its carbohydrate moiety. However, there is only one human IFN-β gene, which encodes a protein of 166 amino acids. IFN-β has low homology to IFN-α, sharing about 30-40% identity.

In contrast to the singleness of the IFN-β gene, HuIFN-α is a subgroup, consisting of a multigene family of 14 genes in essence. Minor variants made of one or two amino acid differences account for the multiple alleles (10). Excluding the pseudogene IFNAP22, there are 13 genes, encoding 13 proteins. Each protein comprises 165-166 amino acids. The protein encoded by gene IFNA13 is identical to protein IFNA1. Thus there are 12 individual interferon alpha proteins: IFNA1, IFNA2, IFNA4, IFNA5, IFNA6, IFNA7, IFNA8, IFNA10, IFNA14, IFNA16. IFNA17, and IFNA21. Amino acid sequence identity among IFN-α subtypes has generally 80-85% homology (11).

Mature IFN-ω shows 60% nucleotide sequence homology to the family of IFN-α species but is longer by 6 amino acids at its C-terminal. IFN-ω is more distantly related to interferon-β (shares about 30% sequence homology). Human IFN-ω is not classified in the IFN-α group because it is antigenically distinct from IFN-α and differs in its interaction with the Type I IFN-α receptor (12). IFN-ω is secreted by virus-infected leukocytes as a major component of human leukocyte interferons.

The mature protein of human IFN-ε contains 185-amino acids, sharing about 33% and 37% sequence homology to IFN-α2 and IFN-β respectively (13, 14). The function and biophysical properties of IFN-ε have not been characterized significantly in detail; however, it functions like Type I interferons. IFN-ε may also play a role in reproductive function (15).

IFN-κ, a 180 amino acid human cytokine, is a recently identified Type I IFN. The coding sequence of IFN-κ is ~30% identical to the other Type I interferons found in humans. A distinguishing feature of IFN-κ is the detectable constitutive expression of its transcript in uninduced cells, particularly keratinocytes. IFN-κ may play a role in the regulation of systemic or local immune functions through its effect on cells of the innate immune system (16). However, IFN-κ exhibits low anti-viral activity (17).

Human Type I interferon appears to bind to two-receptor subunits, IFNAR-1 and -2, which are widely distributed on the cell surface of various cell types. Ligand involvement leads to the induction of the phosphorylation of tyrosine kinases TYK2 and JAK-1, which are coupled to IFNAR-1 and -2 respectively. Once phosphorylated, STAT proteins are released from the receptor and form homodimers as well as heterodimers (18, 19). Once released, the dimers of STATA associate with interferon Responsive Factor 9 (IRF-9), a DNA binding protein, forming a complex called IFN-stimulated gene factor-3 (ISGF-3), that migrates into the nucleus. Next, the ISGF-3 complex binds to a DNA element existing in the upstream of all IFN inducible genes. This is the so-called "classical" signal transduction pathway.

New modes of action and biochemical pathways regulated by Type I IFNs are continually being discovered. For example, downstream of PI3K in the signal transduction pathway, nuclear factor kappa-B (NF-kB) and PKC-d, are associated with anti-apoptotic effects observed in neutrophils incubated with IFN-β (20).

More than 300 genes, called interferon induced genes, are responsive to the IFN treatment. The most studied IFN proteins are those with anti-viral properties. For example, the enzyme of the 2,5oligosynthetase family (OAS-1 and -2) catalyzes the synthesis of short oligoadenylates, which bind and activate RNAseL, an enzyme that cleaves viral and celluar RNAs, thus inhibiting protein synthesis. DsRNA-activated protein kinase (PKR) phosphorylates the translation initiation factor eIF2a, also resulting in the inhibition of viral and cellular protein syntheses. More recently, PKR was also was found to be required for the activation of transcription factor NF-κB, a central actor in inflammatory cytokine induction, immune modulation, and apoptosis. Mx (myxovirus-resistance) proteins inhibit the replication of the RNA viruses by either preventing transport of viral particles within the cell, or transcription of viral RNA. RNA-specific adenosine deaminase (ADAR) converts adensine to inosine, thus causing hypermutation of viral RNA genomes (21).

HuIFNs possess a broad spectrum of biological activities including anti-virus, anti-tumor, and immunoregulation functions. The clinical potentials of human interferons have been widely explored, and are summarized below.

With respect to anti-tumor applications, HuIFNs may mediate anti-tumor effects either indirectly by regulating immunomodulatory and anti-angiogenic responses or by directly affecting proliferation or cellular differentiation of tumor cells (22). Interferon therapy has been used in the treatment of various leukemias (23), for instance, hairy cell leukemia (24), acute and chronic myeloid leukemia (25-27), osteosarcoma (28), basal cell carcinoma (29), glioma (30), renal cell carcinoma (31), multiple myeloma (32), melanoma (33), Kaposi's sarcoma (23) and Hodgkin's disease (34). Combination therapy of IFN-α with cytarabine (ara-C), 5-FU, hydroxyura and IL-2 are well studied, mostly showing significantly better results than the HuIFN-α alone (3). Synergistic treatment of advanced cancer with a combination of HuIFNs and temozolomide has also been reported (35).

With respect to anti-virus applications, HuIFNs have been used clinically for anti-viral therapy, for example, in the treatment of AIDS (36), viral hepatitis including chronic hepatitis B, hepatitis C (37, 38), papilloma virus infection (39), herpes virus infection (40), viral encephalitis (41), and in the prophylaxis of rhinitis and respiratory infections (40).

HuIFNs have also been used clinically for anti-bacterial therapy (42), for example, aerosolized HuIFN-γ (43) and HuIFN-α have been used in patients with multidrug-resistant pulmonary tuberculosis (44). HuIFN-γ has been used in the treatment of multidrug-resistant tuberculosis of the brain (45).

HuIFNs have also been used clinically for immunomodulation therapy, for example, to prevent graft vs. host rejection, or to curtail the progression of autoimmune diseases, such as multiple sclerosis (46, 47) and Sjogren's syndrome (48). IFN-β is approved by FDA in the United States for the treatment of multiple sclerosis. Recently it has been reported that patients with multiple sclerosis have diminished production of Type I interferons and interleukin-2 (49). In addition, immunomodulation therapy with HuIFN-α seems to be an effective therapy in chronic myeloid leukemia (CML) patients relapsing after born marrow transplantation (50).

With regard to vaccine adjuvantation, HuIFNs has been used clinically as an adjuvant in the treatment of melanoma (51) and may also be used as an adjuvant or coadjuvant to enhance or simulate the immune response in cases of prophylactic or therapeutic vaccination for many other diseases (52).

HuIFN-α2α was the first angiogenesis inhibitor to be used in clinical trials and was effective in children for the treatment of life-threatening hemangiomas (53, 54). Another clinical indication is giant-cell tumor of the bone. Kaban et al. reported the dramatic regression of a large, rapidly growing, recurrent giant-cell tumor of the mandible (55).

Although HuIFNs have many important clinical applications, they do exhibit significant side effects and other limitations. Most cytokines, including HuIFNs, have relatively short circulation half-lives since they are produced in vivo to act locally and transiently. Since they are typically administered as systemic therapeutics, HuIFNs need to be administered frequently and in relatively large doses. Frequent parenteral administrations are inconvenient and painful. Further, toxic side effects associated with HuIFNs administration are often so severe that some people cannot tolerate the treatment. These side effects are probably associated with systemic administration of high dosages. Further, in clinical studies it has been found that some patients produce antibodies to rHuIFN, which neutralizes its biological activity (56).

Clearly, development of novel interferon proteins with enhanced potency is urgently needed for numerous applications, e.g., anti-cancer therapies, as well as anti-viral, immunotherapy, anti-parasitic, anti-bacterial, or any medical condition or situation where increased interferon activity and/or reduced side effects is required. Overall, it is highly likely that HuIFNs will play a major role in the next generation of novel anti-tumor and anti-viral therapies (10).

It is well know in the art that the most efficient means to improve the pharmaceutical properties of cytokine drugs is to mutate the cytokine protein itself. Various strategies and techniques to mutate interferon peptides have evolved over time. Generally, three strategies are currently used to create HuIFN-α mutants.

The first strategy is to make IFN hybrids. Some researchers have taken advantage of the presence of naturally occurring restriction endonuclease (RE) cleavage sites within IFN-encoding sequences to piece together homologous coding fragments (57, 58). The production of a number of hybrid IFNs has been reviewed by Horisberger and Di Marco (11); this article provides an overview of the process of construction of such molecules. Specific examples of methods for the construction of hybrid interferons are described. Some researchers have taken the advantage of PCR amplification to construct mutant IFN-αs to thereby create specifically-desired nucleic acid fragments and then gain the potential of piecing together new pieces of different IFNs (59). U.S. Pat. No. 6,685,933 (60) also describes PCR amplification techniques to make human IFN hybrids. The interferon hybrids may be created within an interferon subgroup, such as described in U.S. Pat. No. 5,137,720 (61) and U.S. Pat. No. 6,685,933 (60) or among at least two different interferon classification groups, such as described in U.S. Pat. No. 6,174,996 (62) and U.S. Pat. No. 6,685,933 (60). In addition, the parent genes of the hybrid may come from one species (mostly from human), for example, hybrids between HuIFN-α and HuIFN-ω, or from more than one animal species, for instance, hybrids between human and murine interferon-αs (63).

A second strategy to construct interferon mutants is to use site-directed point mutagenesis by introducing changes of one or more nucleotides into IFN DNA molecules (64). Recently, systematic mutation and computational methods are used as a guide for protein mutagenesis (65).

A third strategy for the construction of Type I HuIFNs is to shuffle IFN gene fragments which are created by RE digestion, PCR amplification, chemically synthesis or DNase digestion, followed by PCR to randomly piece the fragments together and then amplify them. The resulting PCR products are in fact a pool of rearranged interferon alpha gene fragments which may be used to construct a DNA library, from which DNA clones with desired phenotypes may be isolated (66). For example, Chang et al have described a method for constructing and screening a HuIFN shuffling library to identify HuIFN derivates with increased anti-viral and antiproliferation activities in mouse cells (67).

Human Interferon alfacon-1 (consensus interferon) is a recombinant non-naturally occurring HuIFN-α with 166 amino acids. It has been generated by assessing the most highly conserved amino acids in each corresponding region based on the known cloned HuIFN-α sequences. It has 89% sequence homology at amino acid level to HuIFN-α2b and a specific anti-viral activity of approximately $10^9$ IU/mg. Human Interferon alfacon-1 has approved for the treatment of chronic HCV infection in patients 18 years or older with compensated liver disease (68).

Although some recombinant interferon proteins are known in the prior art, there is a need for new interferon-like proteins and protein compositions having enhanced biological activities.

SUMMARY OF THE INVENTION

In accordance with the invention, an isolated polynucleotide encoding a protein having human interferon-like biological activities is disclosed. In one embodiment the polynucleotide comprises a nucleotide sequence at least 93% identical to SEQ ID No: 1. In other embodiments the nucleotide sequence is at least 95% identical or at least 98% identical to SEQ ID No: 1.

In one embodiment, the invention comprises a protein selected from the group consisting of proteins each having an amino acid sequence at least 85% identical to SEQ ID No: 2. Preferably the protein is non-naturally occurring and has enhanced anti-viral and anti-proliferative activity in comparison to human interferon alpha 2b (HuIFN-α2b). For example, the protein may have anti-viral activity at least 2 fold greater than HuIFN-α2b and anti-proliferative activity at least 10 fold greater than HuIFN-α2b. In particular embodiments the protein amino acid sequence is at least 90% identical or at least 95% identical to SEQ ID No: 2

The invention encompasses recombinant vectors comprising the sequence of the polynucleotide and host cells containing the vectors. The invention also encompasses polypeptide fragments exhibiting human interferon-like biological activities. The invention further includes protein constructs and other compositions exhibiting interferon-like biological activities, such as conjugates comprising the protein and another moiety, such as an inorganic polymer. The invention further includes methods and uses of the protein and the compositions for therapeutic purposes, for example as anti-viral or anti-cancer agents. The invention may be also be used for treatment of other conditions responsive to interferon therapy.

BRIEF DESCRIPTION OF THE FIGURES

FIG. 1 depicts a complete DNA sequence encoding a novel protein of the invention referred to herein as Novaferon™ (SEQ ID No:1) (A). FIG. 1 also shows the predicted amino acid sequence of Novaferon (SEQ ID No:2) (B), and the alignment of the Novaferon amino acid sequence with the Novaferon DNA sequence(C). The first amino acid, cysteine, in the mature Novaferon protein is designated as residue 1.

FIG. 2 shows nucleotide sequence alignment of the Novaferon gene with the HuIFN-α14 gene (Genebank number: NM_002172)(A) and amino acid sequence alignment of the Novaferon protein with the HuIFN-α14 protein (translated, Genebank number: NM_002172) (B). The first amino acid, cysteine, in the mature Novaferon protein is designated as residue 1. Novaferon shares approximately 93% sequence identity (462/498) with HuIFN-α14 at the nucleotide level and approximately 87% sequence identity (144/166) at the amino acid level. Divergent nucleotides are indicated by a blank in the middle line.

FIG. 3 shows nucleotide sequence alignment of the Novaferon gene with the HuIFN-α2b gene (Genebank number: NM_000605) (A) and amino acid sequence alignment of the Novaferon protein with the HuIFN-α2b protein (translated from HuIFN-α2b gene with Genebank number: NM_000605) (B). The first amino acid, cysteine, in the mature Novaferon protein is designated as residue 1. Novaferon shares approximately 89% sequence identity (445/498) with HuIFN-α2b at the nucleotide level and approximately 81% sequence identity (135/166) at the amino acid level. Divergent nucleotides are indicated by a blank in the middle line.

DETAILED DESCRIPTION

Figure 4:
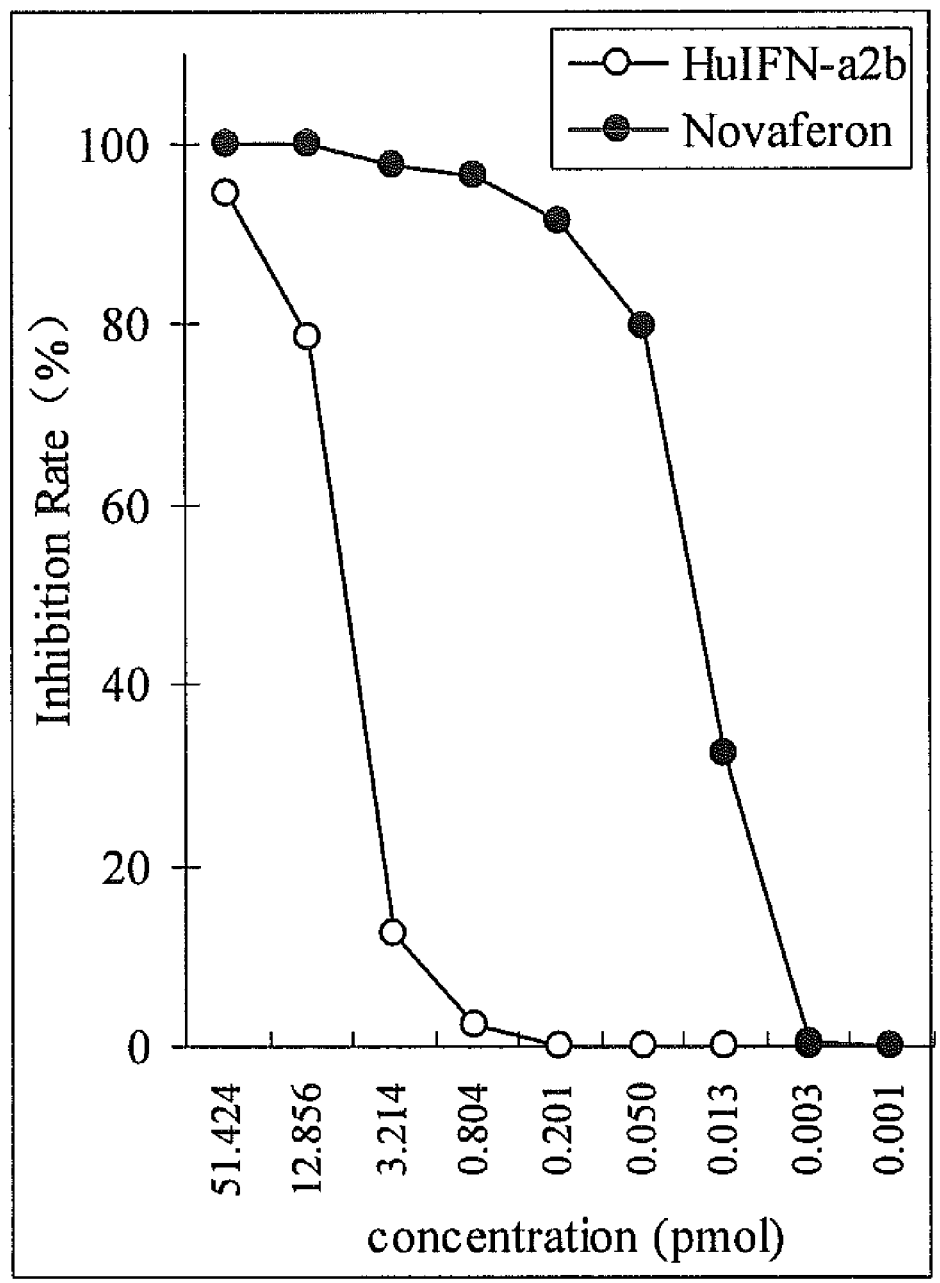
FIG. 4 is a graph showing in vitro anti-proliferative inhibition of Daudi cells by Novaferon in comparison with HuIFN-α2b.

Throughout the following description, specific details are set forth in order to provide a more thorough understanding of the invention. However, the invention may be practiced without these particulars. In other instances, well-known elements have not been shown or described in detail to avoid unnecessarily obscuring the invention. Accordingly, the specification and drawings are to be regarded in an illustrative, rather than a restrictive, sense.

Definition of Terms

Before describing the present invention in detail, it is to be understood that this invention is not limited to the particular protein molecules, methodology, protocols, cell lines, vectors, and reagents described as such may vary. It is also to be understood that the terminology used herein is for the purpose of describing particular embodiments only, and is not intended to limit the scope of the present invention which will be limited only by the appended claims.

In order to make the invention described herein more fully understood, the following terms are employed, and intended to be defined as indicated below. It is to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. All publications mentioned herein are incorporated herein by reference for the purpose of describing and disclosing the cell lines, vectors, and methodologies which are reported in the publications and which might be used in connection with the invention. Nothing herein is to be construed as an admission that the invention is not entitled to antedate such disclosures by virtue of prior invention.

The term "interferon" refers to a family of secreted proteins produced by a variety of eukaryotic cells upon exposure to various environmental stimuli, including virus infection or exposure to a mitogen. In addition to having anti-viral properties, interferons have been shown to affect a wide variety of cellular functions. All interferon units are expressed herein with reference to WHO international standards, 94/786 (rHuIFN-α consensus) and 95/650 (rHuIFN-α2a).

The term "interferon-like" refers to functional and/or structural features exhibited by or similar to known interferons or interferon analogues. For example, "interferon-like biological activities" includes anti-viral and anti-proliferative activities. Other examples of interferon-like biological activities are described herein and would be understood by a person skilled in the art. The plural term "activities" includes the singular term "activity"; that is, the invention encompasses recombinant proteins or other protein constructs or compositions which exhibit at least one interferon-like activity.

The term "consensus interferon" refers to a type of synthetic interferon having an amino acid sequence that is a rough average of the sequences of all the known human alpha interferon sub-types. It has been reported that consensus interferon has a higher (about 5-fold) anti-viral, anti-proliferation and NK cell activation activity than any natural human IFN-α subtype.

The term "isolated" as used herein refers to molecules, such as DNA or RNA, that have been removed from their native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. "Isolated" DNA also includes DNA molecules recovered from a library which may contain natural or artificial DNA fragments of interest, as well as chemically synthesized nucleic acids. Isolated nucleic acids may therefore be recombinantly produced.

The term "nucleotide sequence" refers to a sequence of nucleotides comprising an oligonucleotide, polynucleotide or nucleic acid molecule, and fragments or portions thereof. In the case of a DNA molecule, the sequence may comprise a series of deoxyribonucleotides and in the case of an RNA molecule the sequence may comprise a corresponding series of ribonucleotides. The oligonucleotide, polynucleotide or nucleic acid molecule may be single- or double-stranded and the nucleotide sequence may represent the sense or antisense strand.

The terms "oligonucleotide fragment" or a "polynucleotide fragment", "portion," or "segment" or "probe" or "primer" are used interchangeably and refer to a sequence of nucleotide residues which are at least about 5 nucleotides in length. Preferably the fragments can be used to hybridize to a target nucleotide sequence. A primer serves as an initiation point for nucleotide polymerization catalyzed by either DNA polymerase, RNA polymerase or reverse transcriptase. A fragment or segment may uniquely identify each polynucleotide sequence of the present invention. Preferably the fragment comprises a sequence substantially similar to SEQ ID NO: 1.

The terms "protein" or "peptide" or "oligopeptide" or "polypeptide refer to naturally occurring or synthetic molecules comprising a sequence of amino acids.

The term "open reading frame," or ORF, means a series of nucleotide triplets coding for amino acids without any termination codon and usually denotes a sequence translatable into a protein.

The term "mature protein coding sequence" refers to a sequence which encodes a protein or peptide without a signal or leader sequence. The protein may have been produced by processing in the cell which removes any leader/signal sequence. The protein may be produced synthetically or by using a polynucleotide only encoding only the mature protein coding sequence.

The terms "purified" or "substantially purified" as used herein means that the indicated protein is present in the substantial absence of other biological macromolecules, e.g., other proteins, polypeptides and the like. The protein is purified such that it constitutes at least 95% by weight of the indicated biological macromolecules present (but water, buffers, and other small molecules, especially molecules having a molecular weight of less than 1000 daltons, can be present).

The term "recombinant expression vehicle or vector" refers to a plasmid or phage or virus or vector, for expressing a protein from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionine residue. This residue may or may not be subsequently cleaved from the expressed recombinant protein to provide a final product.

The term "substantial similarity" refers to a nucleic acid or fragment thereof which has a high degree of sequence identity with another nucleic acid when optimally aligned with the other nucleic acid or its complementary strand. The sequence identity or homology may be determined using sequence analysis software, for example. BLASTN. A first nucleic acid is considered to be substantially similar to a second nucleic acid if they show sequence identity of at least about 85-95% or greater when optimally aligned. For example, to determine sequence identity or homology between two different nucleic acids, the BLASTN program "BLAST 2 sequences" is used. This program is available for public use from the National Center for Biotechnology Information (NCBI) over the Internet (http://http://www.ncbi.nlm.nih.gov/blast/b12seq/wblast2.cgi) (69). By way of non-limiting example, such comparisons may be made using the software set to default settings (expect=10, filter=default, open gap=5, extension gap=2 penalties, gap×dropoff=50). Likewise, a first protein or polypeptide is considered to be substantially similar to a second protein or polypeptide if they show sequence identity of at least about 85%-95% or greater when optimally aligned and compared using BLAST software (blastp) using default settings.

By way of further illustration, a polynucleotide having a nucleotide sequence at least, for example, 95% "identical" to a reference nucleotide sequence encoding a protein, means that the nucleotide sequence of the polynucleotide is identical to the reference sequence except that the polynucleotide sequence may include up to five point mutations per each 100 nucleotides of the reference nucleotide sequence encoding the protein. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

The terms "complementary" or "complementarity", as used herein. refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acid strands.

The term "transformation" means introducing DNA into an organism so that the DNA is replicable, either as an extrachromosomal element, or by chromosomal integration. The term "transfection" refers to the taking up of an expression vector by a suitable host cell, whether or not any coding sequences are in fact expressed.

The terms "treatment", "treating" and grammatical equivalents thereof, are used in the broadest sense and include therapeutic treatment, prevention, prophylaxis and amelioration of certain undesired symptoms or conditions.

The terms "biologically activity" and "biological activities" as used herein, refers to structural, regulatory, biochemical or other biological functions in living systems, for example similar or identical to naturally or non-naturally occurring molecules.

The term "anti-proliferation" and "anti-proliferative" as used herein refers to slowing and/or preventing the growth and division of cells, resulting in the reduction of the total cell number and/or reduction the percentage of the target cells in any one or all of the cell cycle phases. Cells may further be specified as being arrested in a particular cell cycle stage: G1 (Gap 1), S phase (DNA synthesis), G2 (Gap 2) or M phase (mitosis). The term "anti-proliferative activity" as used herein refers to the activity of a protein, protein construct, or composition which inhibits cell proliferation, especially neoplastic cell proliferative, e.g., cancer cells, either in vitro or in vivo.

The term "anti-tumor" or "anti-cancer" as used herein refers to counteracting or preventing the formation of malignant tumors. The "anti-tumor activity" or "anti-cancer activity" when used herein refers to the activity of a protein, protein construct, or composition which inhibits cell proliferation, especially neoplastic cell proliferation, e.g., of cancer cells, either in vitro or in vivo.

The term "$IC_{50}$", or the "half maximal inhibitory concentration", represents the concentration of an inhibitor, such as a protein, that is required for 50% inhibition of cell growth in vitro.

The terms "anti-viral" and "anti-virus" as used herein refers to slowing and/or preventing virus infection of cells or interfering with virus replication in cells in vitro and/or in vivo, resulting in slowing or stopping of virus propagation, or reduction in the total number of virus particles. The "anti-viral activity" as used herein means the activity of a protein, protein construct, or composition that inhibits viral infections or interferes with viral replication, either in vitro and/or in vivo.

Novaferon Protein

The present invention relates to the preparation and characterization of a novel human interferon-like protein, referred to herein as "Novaferon"™. As described in detail below, the Novaferon protein exhibits enhanced anti-viral and anti-proliferative biological activities in comparison to naturally occurring HuIFN-α2b as measured in standard in vitro tests. In particular, the Novaferon protein shows a 12.5-fold increase in anti-viral activity when tested in a Wish-VSV system, and about a 400-fold improvement in anti-proliferative inhibition of Daudi cell growth as compared to HuIFN-α2b in the same testing systems.

In one embodiment, the Novaferon protein is encoded by a polynucleotide consisting of 498 nucleotides as shown in SEQ ID No: 1 and FIG. 1(A). The mature Novaferon protein consists of 166 amino acids as shown in SEQ ID No: 2 and FIG. 1(B). The polynucleotide and amino acid sequences and variants thereof which are encompassed by the invention are described in further detail below.

For comparison purposes, the homology of Novaferon with naturally occurring HuIFNs was explored by the inventors. BLAST searches revealed that Novaferon has the highest homology to HuIFN-α14 at both the nucleotide and amino acid levels. As shown in FIG. 2, the polynucleotide sequence (SEQ ID No: 1) encoding Novaferon has a homology of approximately 93% (462/498) to HuIFN-α14 and the amino acid sequence has a homology of approximately 87% (144/166) to HuIFN-α14. In comparison to HuIFN-α2b, the most-widely used human interferon product, the homology is approximately 89% at nucleotide level (445/498) and approximately 81% (135/166) at amino acid level, as shown in FIG. 3.

In regard to synthetic IFN alfacon-1 (consensus interferon), Novaferon has approximately 91% sequence identity at the nucleotide level (453/498) and approximately 84% sequence identity at the amino acid level (140/166).

As described in detail in the experimental section below, the polynucleotide sequence (SEQ ID No: 1) was selected from a DNA shuffling library of Type I human interferon. Briefly, the Novaferon protein was produced by transfection of host cells with a recombinant vector containing the complete polynucleotide sequence of SEQ ID No: 1. The Novaferon protein contained in the supernatant of the host cell-line was purified and shown to exhibit human interferon-like biological activities, such as anti-viral and anti-proliferative functions.

Polynucleotide and Variants

The novel polynucleotide sequence/nucleic acid molecule of the present invention consists of 498 nucleotides as shown in FIG. 1 (SEQ ID No: 1). Using the information provided herein, such as the nucleotide sequence, a nucleic acid molecule of the present invention encoding a Novaferon protein (SEQ ID No: 2) may be obtained by recombinant expression, chemical synthesis or by using other standard molecular biology procedures, such as those for DNA mutagenesis.

The invention, in addition to the isolated nucleic acid molecule (SEQ ID No: 1), also includes DNA molecules having sequences which are different from the DNA sequence disclosed in SEQ ID No: 1 but, due to the degeneracy of the genetic code, still encode the same or substantially the same amino acid sequence of the Novaferon protein (SEQ ID No: 2). The genetic codes and species-specific codon preferences are well known in the art. Thus, it would be routine for one skilled in the art to generate the degenerate variants of DNA sequences different from the DNA sequence of SEQ ID No: 1, for instance, to optimize codon expression for a particular host (e.g., to change codons in the human mRNA to those preferred by a bacterial host such as E. coli).

The invention further provides an isolated nucleic acid molecule having the nucleotide sequence shown in FIG. 1 (SEQ ID No: 1), or a nucleic acid molecule having a sequence complementary to the nucleic acid sequence in SEQ ID No: 1. The present invention also provides information about and relates to the recombinant vectors, which include the isolated nucleic acid molecules of the present invention, and to host cells containing the recombinant vectors, as well as to the methods of making such vectors and creating host cells that express the Novaferon protein, and using the host cells for the production of Novaferon by recombinant techniques.

Based on the nucleic acid sequence of the present invention (SEQ ID No:1, FIG. 1(A), the invention encompasses nucleic acid molecules which are substantially similar thereto, such as nucleic acids having at least about 85-95% or greater sequence identity to SEQ ID No: 1 when optimally aligned. For example, in one aspect nucleic acids having about 93%, 95%, 96%, 97%, 98% or 99% sequence identity to the nucleotide sequence shown in SEQ ID No: 1 are within the scope of the invention, irrespective of whether they encode proteins or polypeptides having biological activities similar to Novaferon (such activities include but are not limited to enhanced anti-viral, anti-proliferative and anti-tumor functions in comparison with HuIFNs). Such nucleic acid molecules could be used, for example, as probes for the detection of mRNA in cells already transfected with a vector containing the nucleotide sequence of the present invention for the production of Novaferon. In another words, these nucleic acid sequences at least about 93%, 95%, 96%, 97%, 98% or 99% identical to the sequence shown in SEQ ID No: 1 could be used as markers for determining the expression of the heterologous genes in a host cell.

Further, the invention includes a polynucleotide comprising any portion of at least about 30 contiguous nucleotides, preferably at least about 50 contiguous nucleotides, of SEQ ID No: 1.

More generally, this invention includes and covers the fragments of any and all isolated nucleic acid molecules that are identical to the partial sequence(s) of the nucleotide sequence shown in FIG. 1 (SEQ ID No: 1). In one embodiment such fragments may be at least about 15 nucleotides in length and are useful as diagnostic probes and primers as discussed herein. Furthermore, this invention includes and covers larger fragments that are about 50 nucleotides or longer in length.

In addition to the nucleic acid sequence disclosed in SEQ ID No: 1 encoding the Novaferon protein, the present invention also includes but is not limited to nucleic acid sequences that encode the amino acid sequence of the complete Novaferon protein together with extra amino acids/peptide(s)/polypeptide(s), for example an added secretory leader sequence.

Also included in the invention are the sequences of nucleic acids that have the nucleic acid sequence disclosed in SEQ ID No: 1 as well as additional, non-coding sequences, including, for example but not limiting to, introns and non-coding 5' and 3' sequences, such as the transcribed, non-translated sequences that play a role in transcription, mRNA processing (i.e. splicing and polyadenylation signals, ribosome binding and stability of mRNA), and additional coding sequences which encode additional amino acids with or without functionalities.

The present invention further relates to the variants of the nucleic acid molecules of the present invention (SEQ ID No: 1), which encode portions, analogs or derivatives of the Novaferon protein. Variants may be obtained by screening an interferon shuffling library or using mutagenesis techniques or/and other known techniques described in the art.

As explained above, such variants may include those produced by nucleotide insertions, deletions or substitutions. The insertions, deletions or substitutions may involve one or more nucleotides. These mutations may occur at the 5' or 3' terminal positions of the reference nucleotide sequence or anywhere between those terminal positions, interspersed either individually among nucleotides in the reference sequence or in one or more contiguous groups within the reference sequence. Alterations may produce conservative or non-conservative amino acid substitutions, deletions or additions. Especially preferred among these are silent substitutions, additions and/or deletions, which do not alter the properties and activities of the Novaferon protein or portions thereof. Also especially preferred in this regard are conservative substitutions.

One aspect of the invention provides an isolated nucleic acid molecule comprising a polynucleotide having a nucleotide sequence at least 93% identical, and more preferably at least about 95%, 96%, 97%, 98% or 99% identical to a polynucleotide selected from the group consisting of: (a) a nucleotide sequence encoding the Novaferon protein having the complete amino acid sequence in SEQ ID No: 2 (i.e., positions 1-166 of SEQ ID No: 2); and (b) a nucleotide sequence encoding a biologically active fragment of the protein of (a); and (c) a nucleotide sequence complementary to any of the nucleotide sequences in (a) or (b) above.

Due to the degeneracy of the genetic code, one with ordinary skill in the art will immediately recognize that a large number of the nucleic acid molecules having a sequence at least about 93%, 95%, 96%, 97%, 98%, or 99% identical to the nucleic acid sequence of the nucleic acid sequence shown in FIG. 1 (SEQ ID No: 1) will encode a protein having activity similar or identical to the Novaferon protein. In fact, since degenerate variants all encode the same protein, this will be clear to the skilled artisan even without perfonning a comparison assay. It will be further recognized in the art that, for such nucleic acid molecules that are not degenerate variants, a reasonable number will also encode a protein having interferon-like biological activities. This is because the skilled artisan is fully aware of amino acid substitutions that are either less likely or not likely to significantly affect protein function (e.g., replacing one aliphatic amino acid with a second aliphatic amino acid), as further described below. For example, guidance concerning how to make phenotypically silent amino acid substitutions is provided by Bowie et al (70), wherein the authors indicate that many proteins are tolerant of amino acid substitutions.

Protein and Polypeptide Variants and Constructs

The present invention encompasses the Novaferon protein of SEQ ID:2 and proteins or polypeptide variants which are substantially similar thereto, such as non-naturally occurring proteins having at least about 85-95% or greater amino acid sequence identity to SEQ ID No: 2. For example, non-naturally occurring proteins having at least about 85%, 90%, 95%, 96%, 97%, 98% or 99% sequence identity to the amino acid sequence shown in SEQ ID No: 2 are within the scope of the invention. Further, the Novaferon protein of the invention may be structurally modified by fusing it to other proteins or protein fragments or other molecules for the purpose of enhancing its functions and properties. Examples include but are not limited to fusing it to other proteins/protein fragments to increase its expression or to further stabilize the Novaferon protein.

In one embodiment, the Novaferon-encoding nucleic acid sequence and/or Novaferon proteins of the invention may be labeled with a label other than the scaffold. "Labeled" herein means that a compound of the nucleic acid sequence (SEQ ID No: 1) or the Novaferon protein (SEQ ID No: 2) has been attached with at least one element, isotope or other chemicals (labels) to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Once made, the Novaferon protein may also be covalently modified. One type of covalent modification includes treating the Novaferon protein with an organic derivatizing agent that is capable of reacting with selected side chains or the N-or C-terminal residues of the Novaferon protein. Derivatization with bifunctional agents is useful, for instance, for crosslinking the Novaferon protein to a water-insoluble support matrix or surface for use in the purification of anti-Novaferon antibodies or screening assays. Commonly used crosslinking agents include 1,1-bis(diazoacetyl)-2-phenylethane, glutaraldehyde, N-hydroxysuccinimide esters (for example, esters with 4-azidosalicylic acid), homobifunctional imidoesters including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications of the Novaferon protein include: deamidation of glutaminyl and asparaginyl residues to the corresponding glutamyl and aspartyl residues, respectively; hydroxylation of proline and lysine; phosphorylation of hydroxyl groups of seryl or threonyl residues; methylation of the amino groups of lysine, arginine, and histidine side chains (71); acetylaffon of the N-terminal amine; and amidation of any C-terminal carboxyl group.

Another type of covalent modification of the Novaferon protein of the present invention comprises altering the native glycosylation pattern of the protein. This may be achieved, for example, by (1) deleting and/or adding one or more carbohydrate moieties found in the native sequence of the Novaferon protein, or(2) adding and/or deleting one or more glycosylation sites that do not exist in the native sequence of the Novaferon protein.

Addition of glycosylation sites to Novaferon protein may be accomplished by altering the amino acid sequence of the Novaferon protein. The alteration may be made, for example, by the addition of, or substitution by, one or more serine or threonine residues to the native sequence of the Novaferon protein (for O-linked glycosylation sites). The alternation of the amino acid sequence of the Novaferon protein could be achieved through changes at the DNA level, particularly by mutating the DNA sequence encoding the Novaferon protein at pre-selected nucleotide bases so that the altered codons would translate into the desired amino acids.

Another means of increasing the numbers of carbohydrate moieties on the Novaferon protein is by chemical or enzymatic coupling of glycosides to the protein. Such methods are described in the art, for example, as early as 1981, Aplin J D and Wriston J C Jr. had described the preparation, properties, and applications of carbohydrate conjugates of proteins and lipids (72).

Removal of carbohydrate moieties presented on the Novaferon protein may be accomplished chemically or enzymatically or by mutational substitution of the codons that encode the amino acid residues that serve as targets for glycosylation. Chemical deglycosylation techniques are known in the art and described, for instance, by Edge A S et al. (73). Enzymatic cleavage of carbohydrate moieties on polypeptides can be achieved by the use of a variety of endo-and exo-glycosidases as described by Thotakura et al (74).

Such derivatized constructs may include moieties improving the solubility, absorption, permeability across the blood brain barrier, biological half life, etc. Such moieties or modifications of Novaferon protein may alternatively eliminate or attenuate any possible undesirable side effects of the protein and the like. Moieties capable of mediating such effects are disclosed, for example, in Remington: The Science and Practice of Pharmacy. (75).

Another type of covalent modification of Novaferon comprises linking the Novaferon protein to one of a variety of non-proteinaceous polymers, e.g., polyethylene glycol, polypropylene glycol, or polyoxyalkylenes, for example in the manner set forth in U.S. Pat. No. 4,640,835 (76); U.S. Pat. No. 4,496,689 (77); U.S. Pat. No. 4,791,192 (78) or U.S. Pat. No. 4,179,337 (79).

Further, the Novaferon protein of the present invention may also be modified in a way to form chimeric molecules comprising a Novaferon protein fused to another heterologous polypeptide or amino acid sequence. In one embodiment, such a chimeric molecule comprises a fusion compound of a Novaferon protein with a tag polypeptide which provides an epitope to which an anti-tag antibody can selectively bind. The epitope tag is generally placed at the amino- or carboxyl-terminus of the Novaferon protein. The presence of such epitope-tagged forms of a Novaferon protein can be detected using an antibody against the tag polypeptide. Also, provision of the epitope tag enables the Novaferon protein to be readily purified by affinity purification using an anti-tag antibody or another type of affinity matrix that binds to the epitope tag. In an alternative embodiment, the chimeric molecule may comprise a fusion compound of a Novaferon protein with an immunoglobulin or a particular region/fragment of an immunoglobulin. For example, to form a bivalent form of the chimeric molecule, the Novaferon protein could be fused to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 (80); the c-myc tag and the 8F9, 3C7, 6E10, G4, B7 and 9E10 antibodies thereto (81); and the Herpes Simplex virus glycoprotein D (gD) tag and its antibody (82). Other tag polypeptides include the Flag-peptide (83); tubulin epitope peptide (84) and the T7 gene 10 protein peptide tag (85).

Furthermore, the Novaferon protein of the present invention can be produced by chemical synthetic procedures known to those of ordinary skill in the art. For example, polypeptides up to about 80-90 amino acid residues in length may be produced on a commercially available peptide synthesizer model 433A (Applied Biosystems, Inc., Foster City. Calif. US). Moreover, the longer chemically synthesized peptides up to 120 residues are also commercially available, for example, from Bio-synthesis, Inc. Lewisville, Tex. USA). Thus, as will be readily appreciated, the full-length mature Novaferon protein can be produced synthetically (for example, in fragments which may then be connected together).

Therefore, the Novaferon protein of the present invention (SEQ ID No: 2) includes all the protein and polypeptide preparations and constructs that have the same amino acid sequence disclosed in SEQ ID No: 2, despite whether these Novaferon proteins and protein derivatives are produced by chemically-synthetic procedures, and/or by recombinant techniques from prokaryotic or eukaryotic host cells or other cells and hosts, including but not limiting to bacterials, yeasts, plants, insects and mammalian cells. Depending on the hosts employed in a recombinant production method, the proteins of the present invention may be glycosylated or non-glycosylated, pegylated or non-pegylated. In addition, proteins of the invention may also include an initial modified methionine residue, in some cases as a result of host-mediated processes. Thus, it is well known in the art that the N-terminal methionine encoded by the translation initiation codon is generally removed, with high efficiency, from any proteins after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Production

The present invention also relates to the recombinant vectors which consist of the isolated DNA molecules of the present invention, to host cells which are genetically engineered/transfected with the recombinant vectors, and to the production of the Novaferon protein or fragments thereof by recombinant techniques. The vector may be, for example, a plasmid, phage, viral or retroviral vector. Retroviral vectors may be replication competent or replication defective. In the latter case, viral propagation generally will occur only in complementing host cells. Examples describing in detail the production of Novaferon are set forth below.

Preferred vectors for the expression of the Novaferon protein of the present invention include, but are not limited to, vectors comprising cis-acting control regions effective for expression in a host operatively linked to the polynucleotide to be expressed. Appropriate trans-acting factors are supplied either by the host, by a complementing vector or by the vector itself upon introduction into the host.

The nucleic acid sequence disclosed in present invention (SEQ ID No: 1) may be operatively linked to an appropriate promoter. "Promoter" herein means any nucleic acid sequences capable of binding RNA polymerase and initiating an extron (usually at the downstream (3')) transcription of the coding sequence for the Novaferon protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. The preferred bacteria promoters include, but are not limited to, *E. coli* laci, trp, phoA and lacZ promoters, the T3 and T7 promoters, the gpt promoter, the lambda PR, PL promoters and the trp promoter Eukaryotic promoters have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter also contains an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter. Preferred animal cell promoters include, but are not limited to, adenovirus major late promoter, herpes simplex virus promoter, and the CMV promoter. Among known eukaryotic promoters suitable in this regard are the CMV immediate early promoter, the elongation factor 1 alpha (EF1A) promoter, the HSV thymidine kinase promoter, the early and late SV40 promoters, and the promoters of retroviral LTRs, such as those of the Rous sarcoma virus ("RSV"). Preferred promoter sequences for expression in yeast include the inducible GAL1/10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene.

Vectors for propagation and expression also generally include one or more selectable markers. Such markers may be suitable for amplification or the vectors may contain additional markers for this purpose. In this regard, the expression vectors preferably contain one or more selectable marker genes to provide a phenotypic trait for the selection of the transfected host cells, although those skilled in the art will recognize that certain system-selectable markers may be provided on separate vectors. Preferred markers include, for example, ampicillin (Amp), tetracycline (Tet) or hygromycin (HYG) resistance genes for culturing in *E. coli* and other bacterias. Yeast-selectable markers include ADE2, HIS4, LEU2, TRP1, and ALG7, which confer resistance to tunicamycin; the neomycin phosphotransferase gene, which confers resistance to G418; and the CUP1 gene, which allows yeast to grow in the presence of copper ions. Animal cell-selectable makers include dihydrofolate reductase (DHFR) gene, neomycin (Neo) or hygromycin (HYG) resistance genes.

Further, vectors for propagation and expression commonly contain one or more sites for transcription initiation, termination and, in the transcribed region, a ribosome binding site for translation. The coding portion of the transcripts expressed by the constructs preferably includes a translation initiating codon at the beginning and a termination codon (UAA, UGA or UAG) appropriately positioned at the end of the DNA sequence to be translated. Selection of promoters, terminators, selectable markers, vectors and other elements is a matter of routine design within the level of ordinary skill in the art. Many such elements are described in the literature and are available through commercial suppliers.

The following vectors are commercially available, and are preferred for use in bacterias: pBV220 (86) and its derivates from Shanghai Sangon; pQE series from Qiagen; pET vectors from Qiagen; pBS vectors, Phagescript vectors, Bluescript vectors, pNH8A, pNH16a, pNH18A, pNH46A from Stratagene; and ptrc99a, pKK223-3, pKK233-3, pDR540, pRIT5 from Pharmacia. Among preferred eukaryotic vectors are pCI vectors from Promega, pcDNA vectors from Invitrogen, pSV2CAT, pOG44, pXT1 and pSG from Stratagene; and pSVK3, pBPV, pMSG and pSVL from Pharmacia. These vectors are listed solely as examples to demonstrate that many commercially available and well known vectors are available to those of skill in the art for use in the production of the Novaferon protein disclosed in the present invention by genetic/recombinant methods.

In certain preferred embodiments in this regard, the vectors provide means for specific expression. Such specific expression may be inducible expression or expression only in certain types of cells or may be both inducible and cell-specific. Particularly preferred among inducible vectors are vectors that can be induced to express by environmental factors that are easy to manipulate, such as temperature and nutrient additives. A variety of vectors suitable for this application, including constitutive and inducible expression vectors for use in prokaryotic and eukaryotic hosts, are well known and employed routinely by those of skill in the art.

The vector containing the DNA sequence disclosed in SEQ ID No: 1, for instance, as well as an appropriate promoter, and other appropriate control sequences, may be introduced, using a variety of art-known techniques, into an appropriate host cell suitable for the expression of a desired protein. Representatives of such suitable hosts include bacterial cells, such as *E. coli, Bacillus subtilis, Streptomyces* cells; yeast cells, such as *Pichia pastoris* cells; insect cells, such as *Drosophila* S2 and *Spodoptera* Sf9 cells; mammalian cells such as CHO and COS; and plant cells. Hosts for a great variety of expression constructs are well known, and those of skill art will be able, with the information disclosed in the present invention, to readily select a host for expressing the Novaferon protein disclosed in SEQ ID No: 2.

Host cells can be genetically engineered to incorporate Novaferon-encoding polynucleotides and express Novaferon proteins of the present invention. For instance, Novaferon-encoding polynucleotides may be introduced into host cells using art-known techniques of transfection. Such methods are described in many standard laboratory manuals, such as those discussed by Kingston (87). Novaferon-encoding polynucleotides may be introduced/transfected alone or with other polynucleotides. Such other polynucleotides may be introduced independently, co-introduced or introduced jointly with the Novaferon-encoding polynucleotides disclosed in SEQ ID No: 1.

For example, Novaferon-encoding polynucleotides of the invention may be transfected into host cells together with a separate polynucleotide encoding a selectable marker for co-transfection and selection of the marker in mammalian cells. Alternatively, the Novaferon-encoding polynucleotides may be incorporated into a vector containing a selectable marker-encoding DNA sequence for inducing propagation in the host cells.

The engineered host cells transfected with the vectors containing the Novaferon-encoding polynucleotide can be cultured in conventional nutrient media which may be modified specifically for activating promoters, selecting transformants or amplifying the target genes. Culturing conditions such as temperature, pH, etc. are adjusted and suitable for the selected host cells to express the Novaferon protein of the present invention.

Suitable secretion signals may be incorporated and co-expressed with the Novaferon protein for promoting the secretion of the translated protein polypeptide into the lumen of the endoplasmic reticulum, into the periplasmic space or into the extracellular environment.

Purification

A suitable host cell type is usually selected for the expression of the target recombinant protein, depending on the nature of the target protein and consideration of other conditions, such as the production costs, whether to scale up easily, size of industrial production, etc. The clones of the transfected cells that express the target protein with the highest yield are then selected, and the final clone with the optimal expression is named the target protein-expressing cell line and used for the production of the target protein. The cell line expressing the target protein is grown in a medium containing various nutrients. For optimal growth of the cells and/or optimal expression of the target protein, various agents or conditions are used to induce the selective promoter incorporated with the cDNA sequence of the target protein in the transfected vector. If the host cell type/expression system is bacteria, the cultured cells are harvested from the medium, typically by centrifugation. The bodies of the harvested cells are broken by physical or chemical means, and the harvested crude extracts, which contain the synthesized target protein, are retained for further purification of the protein. The methods applied to the disruption of the microbial cells include but are not limited to freeze-thaw cycling, sonication, mechanical disruption, or use of cell lysing agents. Such methods are well known to those skilled in the art.

The inventors used the bacteria, E. coli, as the host cell for the expression of recombinant Novaferon protein. As described below, E. coli. was transfected with the vector that contained the Novaferon-encoding polynucleotide sequence, and one strain of E. coli. that had the optimal expression of the Novaferon protein was selected for the production of Novaferon protein. Once synthesized, the protein may be retained in the cytoplasm as insoluble granules, or may be secreted into the cytoplasm in soluble form. In the former case, the granules are recovered after the lysis of the cell bodies, and denatured using, for example, guanidine isothiocyanate or urea. The re-folding of the denatured polypeptide/Novaferon protein is then obtained by diluting the denaturant with excessive dilute solution or by dialysis against a solution of urea and a combination of reduced and oxidized glutathione, followed by dialysis against a buffered saline solution. In the latter case, the protein can be directly recovered, without denature, from the periplasmic space in the soluble and functional form following the disruption of the harvested cells. By avoiding the denaturing and re-folding procedures, the soluble Novaferon protein is not damaged and contains no deformed or mis-folded protein molecules.

The inventors found that a significant portion of the synthesized Novaferon protein produced in the E. coli cell line was secreted into the cytoplasm. This portion was then purified as described below.

Activity Assays and Medical Uses

As indicated above, the Novaferon protein shows sequence homology to many members of the interferon family, in particular to the interferon protein translated by the mRNA of HuIFN-α14 (FIG. 2). HuIFN-α has been shown to have a wide range of biological activities including anti-viral, anti-proliferative, and immunomodulation activities (10).

With such homology to HuIFN-α, Novaferon would be expected to exhibit similar biological functions as HuIFN-α, including but not limiting to, the inhibition of tumor proliferation, anti-viral activities, NK cell activation, and immune system modulation. Of particular importance is not only the retaining of the HuIFN-α-like functional properties but also the enhanced potency of these biological functions of the Novaferon protein in comparison with HuIFN-α. To verify and determine the potency of its functional properties, the biological activities of Novaferon protein were thus determined using the classic and routine in vitro assays designed to detect the anti-viral and anti-proliferative properties. As described in the experimental section below, the in vivo potency of anti-proliferative properties of the Novaferon protein was further observed in animal models of various human cancer types and compared to HuIFN-α as well as to a chemical anti-cancer agent in some experiments.

Many suitable assays for determining the activities of HuIFN are well known in the art. The inventors employed the in vitro cell-based assay systems to determine the anti-viral and anti-proliferative activities. The same in vitro assays were used for all the procedures and experiments related to the present invention, which included but not limited to screening the human Type I interferon gene shuffling library, selecting Novaferon from the expressed proteins of the human Type I interferon gene shuffling library, and the determination of the biological activities of the pure recombinant Novaferon protein.

There are many assays that measure the anti-viral activities of the testing samples/agents by observing the degree of resistance of cells to viruses (88). Three principal bioassays have been used for measuring the anti-viral activities of HuIFN and their hybrids. They are classified according to the methods of determining the various aspects of virus on cultured cells.

The assay for determining the inhibition of virus-induced cytopathic effects measures the degree of reduction of virus-induced lytic cytopathic effects on the cultured cells with pre-treatment of IFN. This assay can be performed in 96-well plates (89), and has been widely used for recombinant HuIFN-α since it provides a simple method for screening a large number of samples.

The inhibition of virus plaque formation is another method of quantifying the anti-viral activities of HuIFN in tissue cultures. The results of a plaque-reduction assay are independent of the multiplicity of infection. Moreover, a 50% reduction in plaque formation is measurable with high precision. Using the ubiquitous vesicular stomatitis virus (VSV) to induce the plaque formation, for instance, it could determine the profile of cross-species activity of a particular recombinant IFN by screening a number of cell lines from different animal species (90).

The third assay is based on the determination of the reduction of virus yield. Virus production is measured, usually during a single cell growth cycle, by the amount of virus released. This assay is particularly useful for testing the anti-viral activities of IFN against viruses that do not cause cytopathic effects, or that do not build plaques in target-cell cultures. In this test, however, the multiplicity of infection affects the apparent degree of protection induced by a fixed concentration of IFN (91).

The anti-viral activities of Novaferon were measured by a standard cytopathic effect-inhibition assay using WISH cells and vesicular stomatitis virus (VSV). Anti-viral activities were determined and calibrated by using the standard reference samples of WHO international standards: 95/650 (rHuIFN-α2a) and 94/786 (rHuIFN-α consensus). One unit of anti-viral activity is defined as the amount of protein needed to achieve 50% inhibition of the cytopathic effects of VSV on cultured cells. As described further below, the activity of Novaferon protein was $2.5 \times 10^9$ IU/mg, which is about 12.5-fold greater than that of HuIFN-α2b. These tests demonstrate that the anti-viral properties of Novaferon are greatly enhanced in comparison to HuIFN-α2b. This increased potency against virus, exhibited by Novaferon protein, provides the basis for a predicting enhanced anti-virus effects in vivo in humans. Based on the nature of HuIFNs, it is reasonable to expect a very broad anti-virus profile for Novaferon. In another words, Novaferon should be more potent toward a wide range of viruses than natural HuIFNs. The increased anti-virus potency of Novaferon could be translated into better anti-virus effects or better therapeutic effects in clinical setting for patients with various viral diseases.

As explained above, IFNs also inhibit cell proliferation and exhibit potent anti-tumor effects through a variety of mechanisms. Several in vitro anti-proliferation tests have been established by using cell culture systems, and are well described in the art. Cell proliferation in these assays can be measured by counting cell numbers; crystal violet bioassay (92, 93); chemosensitivity to neutral red dye (94~96); incorporation of radiolabelled nucleotides (97); incorporation of 5-bromo-2'-deoxyuridine (BrdU) in the DNA of proliferating cells (98); use of tetrazolium salts (99, 100).

The human lymphoblastoid Daudi cell line is very sensitive to the anti-proliferation effect of HuIFN-α, and its growth in suspension cultures facilitates the quantification of its cell numbers (101). This cell line has been used for measuring the anti-proliferation activity of HuIFN-α and hybrids for many years (102). Other cell lines are also used for testing the anti-proliferation activity of a testing agent.

The anti-proliferative activities of Novaferon protein were observed in vivo by observing the inhibition of the tumor mass growth by Novaferon administration to animal models with various human tumor xenografts. The in vivo anti-tumor effects of Novaferon was compared with HuIFN-α2b and in some xenograft models, with chemical anti-tumor agent as well.

As described in detail below, the inventors found that the in vitro anti-proliferative activity of Novaferon, measured by using standard Daudi cell method, was 400-fold more potent than natural HuIFN-α2b, which exhibits probably the most potent anti-proliferative activities among all natural HuIFNs. The increased anti-proliferative potency of Novaferon was broad and universal, as it exhibited more potent or enhanced inhibition, than natural HuIFN-α2b, of all the human cancer cell lines the inventors tested in vitro. This indicates that the potent inhibition of human cancer by Novaferon is not selective. Although the extent of its enhanced anti-proliferative activities toward all the tested types of human cancer cell lines varied, Novaferon has the potential to be a broad anti-cancer agent in clinical setting. This is a significant advantage over chemical anti-cancer agents, monoclonal antibodies and other target-specific anti-cancer agents.

The xenograft animal model experiments described below further establish that:
  (1). The in vivo anti-proliferation effects of Novaferon were greatly enhanced or more potent in comparison to natural HuIFN-α2b
  (2). The in vivo anti-proliferation effects of Novaferon, at much lower doses, were better than the tested chemical agent, 5-Fluorouracil (5-FU) in the same xenograft model.
  (3). Novaferon was able to achieve over 90% inhibition of cancer growth in the xenograft models, but did not induce weight loss, activity changes and other negative side-effects in the treated animals, which was in sharp contrast to the significant weight loss and activity reduction in the 5-FU-treated animals.

These results indicate that the in vitro and in vivo anti-proliferative properties of Novaferon are greatly enhanced, comparing to natural HuIFN-α2b. The increased anti-proliferative potency of Novaferon is translated into effective inhibition (>90%) of human tumor growth in a mouse animal model, and this inhibition seems to work very broadly to all the types of human cancers tested and better than the classic chemical anti-cancer agent, 5FU. These results also indicate that the potent inhibition of cancer cell growth by Novaferon is very specific toward the cancer cell but not toward the normal cells as supported by the observation of normal eating and activity behavior and no weight loss in Novaferon-treated animals. Novaferon thus has the potential to work on all or majority of human cancers.

In a preferred embodiment, the complete or partial molecule (s) of Novaferon protein (SEQ ID No: 2), made by recombinant technologies using the polynucleotide sequence of SEQ ID No. 1 or chemically synthesized, could be applied to the treatment and/or prevention of any and/or all of the tumors and cancers of human-origin or non-human-origin, in humans and/or non-human species. These tumors, for example, include but are not limited to, osteogenic sarcoma; multiple myeloma; Hodgkin's disease; nodular, poorly differentiated lymphoma; acute lymphocytic leukemia; acute myeloid leukemia; breast carcinoma; melanoma; papilloma; and nasopharyngeal carcinoma, colon cancer, liver cancer and melanoma.

In another embodiment, the complete or partial molecule (s) of Novaferon protein (SEQ ID No: 2), made by recombinant technologies using polynucleotide sequence of SEQ ID No: 1 or chemically synthesized, could be applied to the treatment and/or prevention of any and/or all of the viral diseases in humans and/or non-human species. Examples of the susceptible viral infections include, but are not limited to, viral encephalomyocarditis, influenza and other respiratory tract viral infections, rabies and other viral zoonoses, and arbovirus infections, as well as herpes simplex keratitis, acute hemorrhagic conjunctivitis, varicella zoster, and hepatitis B and C, SARS and bird flu, human immune deficiency syndrome (AIDS, HIV).

In another embodiment, the complete or partial molecule (s) of Novaferon protein (SEQ ID No: 2), made by recombinant technologies using polynucleotide sequence of SEQ ID No: 1 or chemically synthesized, could be applied to the treatment and/or prevention of any and/or all of the immune system-related disorders in humans. Examples of the immune disorders include but are not limited to rheumatic arthritis, multiple sclerosis, and Sjogren's syndrome diabetes. The Novaferon protein may also be applied to preventing graft vs. host rejection as well.

In another embodiment, the complete or partial molecule (s) of Novaferon protein (SEQ ID No: 2), made by recombinant technologies using polynucleotide sequence of SEQ ID No: 1 or chemically synthesized, could be applied to the treatment and/or prevention, as an immunoadjuvant, for any and/or all of the angiogenesis diseases. Example of the angiogenesis diseases include but are not limited to hemangiomas, tumor-induced neovasculature, age-related macular degeneration and diabetic retinopathy.

The Novaferon protein, alone or together with any other proteins/carrier materials or other constructs, may be administered to humans and/or non-human species in any pharmaceutically acceptable preparations/formulations in any administration/delivery pathways/methods, which include but are not limited to the oral intake, inhalation, intranasal spray, intraperitoneal, intravenous, intramuscular, intralesional, or subcutaneous injection.

Pharmaceutical preparations/formulations containing the Novaferon protein as the active ingredient could be made by incorporating an appropriate solid or liquid carrier, in the forms of liquid, solid, semi-solid, and/or any other clinically acceptable forms, such as tablets, pills, powders, liquid solutions or suspensions, liposomes, suppositories, injectable, and infusible solutions. The Novaferon-containing preparations/formulations could be made by using the conventional carriers, materials, methods that are described in the art or generally accepted by the practice of pharmaceutical industry. The Novaferon-containing preparations/formulations could also be made by using the non-conventional methods, materials that have not been described in the art nor used by the pharmaceutical industry.

For instance, parenteral formulations are usually injectable fluids that consist of the pharmaceutically and physiologically acceptable materials such as water, physiological saline, other balanced salt solutions, aqueous dextrose, glycerol, etc. In addition, the injectable fluids could also contain, in addition to the Novaferon protein, other proteins as carriers, such as human serum albumin or plasma preparations. The pharmaceutical preparations/formulations may also contain minor amounts of non-toxic auxiliary substances, such as wetting or emulsifying agents, preservatives, and pH buffering agents (for example sodium acetate or sorbitan monolaurate). Methods of formulation are well known in the art and are disclosed, for example, in Remington: The science and Practice of Pharmacy. Phamaceutical Sciences(75).

The particular Novaferon protein preparations/formulations would be determined by the intended clinical applications and/or administration methods, and could be made by any one skilled in the art using known techniques. For instance, in addition to injectable fluids, topical and oral formulations can be employed. Topical preparations can include but are not limited to eye drops, ointments, and sprays. Oral formulations include but are not limited to the forms of liquid (e.g., syrups, solutions or suspensions), or solid (e.g., powders, pills, tablets, or capsules). For solid preparation/formulations, conventional non-toxic solid carriers include but are not limited to the pharmaceutical grades of mannitol, lactose, starch, or magnesium stearate. Actual procedures and/or methods of making these preparations/formulations are known, or will be apparent, to those skilled in the art (75).

The pharmaceutically acceptable preparations/formulations of the Novaferon protein can be administrated to humans and/or non-human species in a variety of ways that include but are not limited to, oral, subcutaneous, intravenous, intranasal, transdermal, intraperitoneal, intramuscular, intrapulmonary, vaginal, rectal, or intraocular delivery, and in the treatment of wounds, directly applied locally.

The concentrations/amounts of the Novaferon protein in the preparations/formulations may vary from >0 to 1.0 molar and/or >0 to 100% (weight/weight) depending on the clinical practice. The exact doses, administration intervals, and the duration of treatment of each and/or all of the Novaferon preparations/formulations will be determined by clinical trials, disease conditions, patient status and health care providers. In a preferred embodiment, due to the protein degradation, systemic versus localized delivery, and rate of new protease synthesis, as well as the age, body weight, general health, sex, diet, time of administration, drug interaction and the severity of the condition, etc., adjustments to the Novaferon administration including but being not limited to the individual and/or total doses, administration intervals, the duration of treatment, and necessary courses of treatment, may be necessary, and will be ascertainable with routine experimentation by those skilled in the art.

In a preferred embodiment, the in circulation half-life of Novaferon protein after administration to the bodies of humans and/or non-human species can be altered. The alternations include but are not limited to the extension or shortening of Novaferon's half-life in vivo. The extension of the in vivo half-life of the Novaferon protein can be achieved in various ways, which include but are not limited to:

(1). Complex formation between a Novaferon molecule and a monoclonal antibody. Such an antibody would preferably connect to the Novaferon protein at sites that do not materially impair its therapeutic functions (103).

(2). Fusion complex of Novaferon with other proteins/polypeptides. Novaferon molecule can be recombinantly fused to other proteins/polypeptides, such as a fragment of the constant region of an immunogloblin (Fc) (104).

(3) Conjugation of Novaferon protein. For example, Novaferon protein can be conjugated with non-antigenic polymers, such as polyethylene glycol or related polyakylene glycol moieties (105-108).

In another preferred embodiment, a therapeutic compound could be conjugated to an antibody, preferably an anti-Novaferon protein antibody. The therapeutic compound may be a cytotoxic agent. In this method, the cytotoxic agents may be targeted, by the binding of the conjugated antibody to Novaferon molecules, to tumor tissue or cells, thereby destroying and the reducing the number of afflicted cells to achieve reduction of cancer symptoms. Cytotoxic agents include, but are not limited to, cytotoxic drugs, toxins or active fragments of such toxins, and radiochemicals. Suitable toxins and their corresponding fragments include diptheria A chain, exotoxin A chain, ricin A chain, abrin A chain, curcin, crotin, phenomycin, enomycin and the like.

In a preferred embodiment, the full length sequence, partial sequences, and/or regulatory sequence of the Novaferon protein-encoding polynucleotide sequence (SEQ ID No: 1) can be used in gene therapy-related administration by anyone skilled in the art. The antisense application, based on the Novaferon protein-encoding polynucleotide sequence (SEQ ID No: 1) can also be used either as gene therapy (i.e. for incorporation into the genome) or as antisense compositions, as will be appreciated by those skilled in the art.

In gene therapy applications, genes are introduced into cells to achieve the in vivo synthesis of the target proteins encoded by these genes. Conventional gene therapy achieves the sustained therapeutic effects by a single treatment or repeated administration of a therapeutically effective DNA or mRNA. On the other hand, antisense RNAs and DNAs can also be used as therapeutic agents for blocking the expression of certain genes in vivo. It has already been shown that short antisense oligonucleotides can be delivered into cells where they act as inhibitors (109).

In a preferred embodiment, the Novaferon protein-encoding polynucleotide sequence (SEQ ID No: 1), in full length or partial length, can be used as DNA vaccines. Naked DNA vaccines are generally known in the art (110). Methods for the applications of the Novaferon-encoding gene (SEQ ID No: 1), full length or partial length, as DNA vaccines are well known to one with ordinary skill in the art, and include but are not limited to placing the Novaferon gene or portion of the Novaferon gene under the control of a promoter for the expression of the full length or partial length of the Novaferon protein in humans and/or non-human species.

EXAMPLES

The following examples serve to more fully describe the manner of using the above described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

Example 1

PCR Amplification of Human IFN-α Genes from Human Leukocyte cDNAs

Total mRNA was extracted from human peripheral blood leukocytes. Preparation of cDNA was preformed using Advantage™ RT-for-PCR Kit (Clontech, Mountain View, Calif., US) and a cDNA synthesis primer (oligo dT18) according to the manufacturer's recommendations.

Amplification of human IFN-α cDNAs was done by PCR technology on a MJ PTC thermal cycler, using the following conditions: 2.5 µl 10× pfx amplification buffer (Invitrogen, Carlsbad, Calif., US), 0.75 µl 10 mM dNTPs, 0.5 µl 25 mM $MgSO_4$, 0.25 µl Platinum pfx DNA Polymerase (2.5 U/µl; Invitrogen, Carlsbad, Calif., US), 0.75 µl cDNA, 0.75 µl 5' primer (10 µM; IFNaO5: 5'-TGGTGCTCAGCT (A/G) CAAGTC-3').(SEQ ID No:3) 0.75 µl 5' primer mixture (1.7 µM each;
IFNaO3-1: 5'-AATCATTTCCATGTTG(A/G)ACCAG-3' (SEQ ID No:4);
IFNaO3-2: 5'-AATCATTTCCCGGTTGTACCAG-3'(SEQ ID No:5);
IFNaO3-3: 5'-AATCATTTCCATGTTGAAACAG-3'(SEQ ID No:6);
IFNaO3-4: 5'-AATCATTTCAAGATGAGCCCAG-3'(SEQ ID No:7);
IFNaO3-5: 5'-AATGATTTTCATGTTGAACCAG-3'(SEQ ID No:8);
IFNaO3-6: 5'-AATCATTT(C/G)(C/G)ATGTTGAACCAG-3'(SEQ ID No:9);
IFNaO3-7: 5'-GATCATTTCCATGTTGAATGAG-3'(SEQ ID No:10):
IFNaO3-8: 5'-GAGTCGTTTCTGTGTTGGATCAG-3' (SEQ ID No:11).

Amplified PCR products were electrophoresed on a 1.0% agarose gel, excised, gel-purified, and were cloned into pCRII-TOPO or pCR-4-TOPO vector (Invitrogen, Carlsbad, Calif., US) according to the manufacturer's recommendations. Automated sequencing was carried out on a Prism Ready Reaction Dye Termination mix on an ABI automated sequencer (PE Applied Biosystems, CA, US).

Since no desired inserts for the IFNa6, IFNa7 and IFNa16 coding sequences were found in above clones, PCRs were conducted again under the above conditions with the exception of type specific primers. For specific amplification of IFNa6, 5' and 3' primers were IFNaO5: 5'-TGGTGCT-CAGCT (A/G)CAAGTC-3'(SEQ ID No:3), and IFNaO3-8: 5'-GAGTCGTTTCTGTGTTGGATCAG-3'(SEQ ID No:11) respectively. For specific amplification of IFNa7, 5' and 3' primers were IFNa7UO: 5'-ATGCCCCTGTCCTTTTCTT-TAC-3'(SEQ ID No:12) and an equal molar mix of IFNaO3-5 and IFNaO3-6, respectively. For specific amplification of IFNa16, 5' and 3' primers used were IFNa7UO and IFNaO3-7: 5'-GATCATTTCCATGTTGAATGAG-3'(SEQ ID No:10) respectively. Amplified fragments were cloned into pCRII-TOPO or pCR-4-TOPO vector and sequenced as above.

All cloned Type I human IFN-alpha genes were individually aligned with those DNA sequences in Genebank. The GeneBank nucleotide accession numbers for these genes referenced herein are: NM_024013(IFN-α1), NM_000605 (IFN-α2), NM_010504 (IFN-α4), NM_010505 (IFN-α5), NM_008335 (IFN-α6), NM_008334 (IFN-α7), NM_008336 (IFN-α8), NM_002171 (IFN-α10), NM_002172 (IFN-α14), NM_002173 (IFN-α16), NM_021268 (IFN-α17), NM_002175 (IFN-α21).

Example 2

Construction of Shuffling Libraries of Type I HuIFN-bearing Plasmids

To construct plasmids bearing the coding sequence of one of the Type I human IFN-αs, 15 pairs of oligonucleotides, with BamHI and EcoRI restriction sites, were synthesized (Genentech, South San Francisco, Calif., US), based on the individual cDNA coding region for mature human Type I IFN proteins. The GeneBank nucleotide accession numbers for these proteins referenced herein are: NM_024013(IFN-α1), NM_000605 (IFN-α2), NM_010504 (IFN-α4), NM_010505 (IFN-α5), NM_008335 (IFN-α6), NM_008334 (IFN-α7), NM_008336 (IFN-α8), NM_002171 (IFN-α10), NM_002172 (IFN-α14), NM_002173 (IFN-α16), NM_021268 (IFN-α17), NM_002175 (IFN α21). The primers and plasmids constructed in Example 1 as templates were used in a standard PCR (111). The resulting products were cleaved with restriction endonucleases (REs) BamHI and EcoRI and cloned into the E. coli expression vector pBVB, which is a derivate expression plasmid of pBV220 (86) containing a BamHI site and an EcoRI site in its multiple cloning region. These final constructs were all verified by DNA sequence analysis (PE Applied Biosystems, US).

DNA fragments containing human IFN ORF were amplified by PCR using a pair of oligonucleotides, BVF4: 5'-AGGGCAGCATTCAAAGCAG-3'(SEQ ID No: 13) and BVR3: 5'-TCAGACCGCTTCTGCGTTCTG-3'(SEQ ID No:14), and by using Type I HuIFN-bearing plasmids constructed previously. The resulting products were mixed in equal amounts and subjected to DNase I digestion and PCR assembly according to the procedure described by Stemmer (112).

The assembled PCR products were further amplified by a pair of inner primers: BVF: 5'-GAAGGCTTTGGGGTGT-GTG-3'(SEQ ID No:15) and BVR: 5'-AATCTTCTCTCATC-CGC-3'(SEQ ID No:16), followed by BamHI and EcoRI digestion and cloned back into the E. coli expression vector pBVB cleaved with REs BamHI and EcoRI. These final constructs were all verified by DNA sequence analysis. The plasmid-bearing shuffled HuIFN-α genes were transformed into E. coli DH5α competent cells.

In all PCR procedures above, either PCR amplification or PCR assembly, regular DNA polymerase (New England Biolab, MA, US), instead of high fidelity DNA polymerase, was used.

Example 3

Screening the Shuffling Libraries

Freshly transformed E. coli DH5α cells were grown overnight on an LB plate at 37° C. Single colonies were individually picked up and inoculated in 100 µl of LB medium containing 50 µg /ml of ampicillin in 96-well plates. Colonies were shaken at 250 rpm at 30° C. After being cultured overnight, 10 µl of bacterial cultures were duplicately inoculated into 100 µl of LB medium containing 50 µg /ml of ampicillin in 96-well plates. The original plates (so called stock plates) were temporarily stored at 4° C. The cells in duplicated plates were grown at 30° C. until OD600 became 0.4 and were then induced by 42° C. After 4-hour's heat induction, bacteria cultures were directly moved into −80° C. freezer for starting the frozen-thaw cycle. After 2 cycles of frozen-thaw, the bacteria suspension/lysate was diluted to a desired concentration and exposed onto Daudi cell culture for an anti-proliferation test (101) or Wish cell culture for an anti-viral test (113).

In each round of screening steps, 20,000 colonies were primarily screened and about 100 colonies with the highest anti-proliferative or anti-viral activities were selected for further confirmative testing. The selected bacterial cultures in stock plates were streaked on LB plates containing 50 µg/ml ampicillin. Single colonies were grown overnight at 37° C., picked, and inoculated in 1 ml of LB medium containing 50 µg/ml of ampicillin in test tubes. Bacteria in tubes were grown overnight at 30° C. with shaking at 250 rpm. Then 40 µl of grown bacteria was inoculated into one of another set of tubes containing 1 ml of LB with ampicillin (50 µg/ml). The samples were then subjected to the steps of induction expression, cell culture harvesting, freeze-thaw cycle treatment and anti-proliferative or anti-viral testing as described above in regard to the primary screening steps.

In each round of screening steps, about 20 colonies with the highest anti-proliferative or anti-viral activity were chosen after confirmative testing to make plasmids and their inserts were sequenced automatically. The inserts having a unique DNA sequence were further amplified by using a pair of PCR primers BVBF: 5'-ACCATGAAGGTGACGCTC-3'(SEQ ID No:17); and BVR: 5'-AATCTTCTCTCATCCGC-3'(SEQ ID No:16), which are flanking sequences at upstream and downstream of multiple cloning sites of pBVB vector respectively. The amplified PCR products were used for the next round of shuffling library construction.

Five cycles of screening steps were performed based on the augment of either anti-proliferative or anti-viral activity.

Example 4

Expression and Purification of Recombinant Novaferon Protein in E. coli

Novaferon protein (SEQ ID No:2) was expressed in E. coli. The reading frame of SEQ ID No: 1 with an artificial addition of initiation codon ATG was cloned into the temperature-inducible pBVB vecter under control of the λPRPL promoter (114). The expression plasmid of Novaferon, pBVBNF, was transformed in DH5α cells. Single colonies were individually picked up and inoculated in 2 ml of LB medium containing 50 µg/ml of ampicillin and incubated at 30° C. for 8 hours. Then the 2 ml of cultured bacteria was further incubated with 50 ml of medium containing 50 µg/ml of ampicillin overnight at 30° C. with agitation. Next morning, the overnightly-cultured bacteria was seeded at a ratio of 1:10~1:20 into a large volume of LB medium containing 50 µg/ml of ampicillin, and incubated at 30° C. with agitation. When the cultures had reached the mid-log phase of growth (A550=0.5–0.6), the incubation temperature was rapidly raised up to 42° C. and kept for 4 hours in order to induce the expression of Novaferon. After 4-hour heat induction, the bacteria cells were centrifuged and washed with PBS (137 mM NaCl, 2.7 mM KCl, 10 mM $Na_2HPO_4$, 2 mM $KH_2PO_4$) 3 times, then stored at −80° C. until proceeding to purification.

Most Novaferon protein molecules were soluble in the E. coli production system described herein, although they were over-expressed in the cytoplasm. Thus, cells were disrupted by lysozme digestion in Cell Lysis buffer I (50 mM Tris-Cl (pH8.0), 1 mM EDTA (pH8.0), 100 mM NaCl) (115). The lysate was further sonicated in order to disrupt the remaining intact cells and splice DNA molecules. Then the lysate was centrifuged.

The soluble Novaferon protein molecules in the supernatants were sequentially purified by hydrophobic, ion exchange chromatography and gel filtration. First, the supernatants were loaded onto and passed through the Phenyl Sepharose 6 Fast Flow Column (GE Healthcare, US). Secondly, the fractions containing Novaferon protein were applied to POROS 50 D Column (Applied Biosystems, US). Thirdly, the fractions containing Novaferon molecules were subject to the purification by POROS 50 HSColumn (Applied Biosystems, US), and finally, the collected Novaferon molecules were further purified by HiLoad 26/100 Superdex 75 pg (Amersham, US).

The purity of the pure Novaferon protein was verified by 15% SDS-PAGE analysis. The pure recombinant Novaferon protein showed as a single band with a molecular weight (MW) of 19-20 KDa. Mass spectrometry analysis indicated that the purity of the purified Novaferon molecule was >98%, and the molecular weight was 19313 dalton, which was identical with the predicted molecular weight 19315 dalton from its amino acid sequence.

Example 5

Expression and Purification of Recombinant HuIFN-α2b in *E. coli*

The expression plasmid of HuIFN-α2b, pBV2b, contains the cDNA coding region for the mature protein of HuIFN-α2b (GeneBank nucleotide accession number: NM_000605), which is under the control of the heat-inducible λ PRPL promoter. The expression of HuIFN-α2b was performed by following the protocols described by Joseph S and David WR (116).

The expression plasmid, pBV2bF, was transformed in DH5-α cells. Single colonies were individually picked up and inoculated in 2 ml of LB medium containing 50 μg/ml of ampicillin and incubated 30° C. for 8 hours. Then the 2 ml of cultured bacteria was further incubated with 50 ml of medium containing 50 μg/ml of ampicillin overnight at 30° C. with agitation. Next morning, the bacteria culture was seeded at a ratio of 1:10~1:20 into a large volume of LB medium containing 50 μg/ml of ampicillin, and incubated at 30° C. with agitation. When the cultures had reached the mid-log phase of growth (A550=0.5–0.6), the incubation temperature was rapidly raised up to 42° C. and kept for 4 hours in order to induce the expression of HuIFN-α2b. After 4-hour's heat induction, the cells were centrifuged and washed with PBS (137 mM NaCl, 2.7 mM KCl, 10 mM $Na_2HPO_4$, 2 mM $KH_2PO_4$) 3 times, then stored at −80° C. until proceeding to purification.

HuIFN-α2b protein was insolubly expressed in the *E. coli* expression system described herein, and thus the inclusion body recovery and washing procedures were conducted according to protocols described in Molecular Cloning (115). Briefly, the harvested bacterial cells were resuspended in Cell Lysis buffer I (50 mM Tris-Cl (pH8.0), 1 mM EDTA (pH8.0), 100 mM NaCl) and lysed by lysozyme and sonication. Inclusion bodies were washed 3 times with ice cold Cell Lysis buffer II (cell lysis buffer I supplemented with 0.5% (v/v) Triton X-100).

Recovered inclusion bodies were broken by suspending in 7N guanidine at room temperature with agitation for 4 hours. Following a 15 minute centrifugation at 4° C., the denatured protein was refolded in 0.15 M pH9.5 Borex buffer for 48 hours at 4° C. The pH was adjusted to 7.4 by HCl at the last step of refolding.

The solution containing refolded HuIFN-α2b was then purified by hydrophobic, ion exchange chromatography and gel filtration. First, the solution was loaded onto and passed through the Phenyl Sepharose 6 Fast Flow Column (GE Healthcare, US). Secondly, the fractions containing HuIFN-α2b were applied to POROS 50 D Column (Applied Biosystems, US). Thirdly, the fractions containing HuIFN-α2b were subject to the purification by POROS 50 HSColumn (Applied Biosystems, US). Finally, the collected HuIFN-α2b molecules were further purified by HiLoad 26/100 Superdex 75 pg (Amersham, US). The pure HuIFN-α2b protein showed as a single band by 15% SDS-PAGE analysis and its purity was >98% as confirmed by Mass spectrometry.

Example 6

Determination of Anti-viral Activity of Novaferon

Anti-viral activity was determined using the WISH-VSV system as described in the classical protocols described by Armstrong J A (113). On the first day, WISH cells (ATCC, catalog No. CCL 25) were seeded in 96-well plates at a density of 14,000 cells/well and incubated at 37° C. 24 hours later, 2-fold serial diluted Novaferon, HuIFN-α2b, WHO human IFN international standards or blank culture medium was added into each well, and incubated at 37° C. for another 24 hours. On the third day, the medium was removed, and replaced with medium containing 1,000 PFU of Vesicular Stomatitis Virus (VSV, ATCC, catalog No.VR-1421). The cells were again incubated for 24 hours at 37° C. and were then washed with 0.85% NaCl to remove dead cells. Next, culture plates were soaked into dye-fixer solution (0.5% crystal violet, 5% formalin (V/V), 50% ethanol (V/V), and 0.85% NaCL) for 1 hour. The dye-fixer solution was then decanted, and the microplates were rinsed copiously with tap water and allowed to dry. The stained cells were dissolved by 0.2 ml of 2-methoxyethanol. The plates were read at 550 nm in a Model Opsys MR (Thermo Labsystems, US) for crystal violet bioassay.

All experiments were preformed in triplicate and the Novaferon and HuIFN-α2b samples were tested in the same plate. The anti-viral activities of Novaferon and HuIFN-α2b prepared herein were assayed in parallel and the anti-viral units (international unit, or IU) were determined with reference to WHO international standards, 94/786 (rHuIFN-α consensus) and 95/650 (rHuIFN-α2a), which were purchased from National Institute for Biological Standards and Control (NIBSC, USA).

The measured anti-viral activity of purified Novaferon protein against VSV on WISH was $2.5 \times 10^9$ IU/mg while the anti-viral activity of HuIFN-α2b is $2.0 \times 10^8$ IU/mg. This data indicates that the anti-viral activity of the Novaferon protein is about 12.5-fold stronger than that of HuIFN-α2b.

Example 7

Anti-proliferative Activity of Novaferon

The anti-proliferative activity assay was performed basically as described by Evinger and Pestka (101).

A. Cell Culture of Human Tumor Cell Lines

The human tumor cell lines were purchased from different organizations (Table 1, below), namely, ATCC (American Type Culture Collection, P.O. Box 1549, Manassas, Va. 20108, USA), DSMZ (German National Resource Centre for Biological Material, Deutsche Sammlung von Mikroorganismen und Zellkulturen GmbH, Mascheroder Weg 1b, 38124 Braunschweig, Germany), JCRB (Japanese Collection of Research Bioresources-Cell Bank, National Institute of Biomedial Innovation, 7-6-8 Saito-Asagi, Ibaraki-shi, Osaka 567-0085, Japan).

TABLE 1

Human Tumor Cell Lines

| Cell lines | Tumors | Codes | Organizations* |
|---|---|---|---|
| A-375 | Melanoma | CRL1619 | ATCC |
| IGR-1 | Melanoma | Acc 236 | DSMZ |
| IGR-37 | Melanoma | Acc 237 | DSMZ |
| IPC-298 | Melanoma | Acc 251 | DSMZ |
| HCT-8 | Colorectal adenocarcinoma | CCL-244 | ATCC |
| SW1116 | Colorectal adenocarcinoma | CCL-233 | ATCC |
| LS 180 | Colorectal adenocarcinoma | CL-187 | ATCC |
| DLD-1 | Colorectal adenocarcinoma | CCL-221 | ATCC |
| LS174T | Colorectal adenocarcinoma | CL-188 | ATCC |
| Hep G2 | hepatocellular carcinoma | HB-8065 | ATCC |

TABLE 1-continued

Human Tumor Cell Lines

| Cell lines | Tumors | Codes | Organizations* |
|---|---|---|---|
| Hep3B | hepatocellular carcinoma | HB-8064 | ATCC |
| HuH-7 | Hepatoma | 0403 | JCRB |
| PLC/PRF/5 | Hepatoma | CRL-8024 | ATCC |
| HL60(S) | lymphocytic | 0163 | JCRB |
| Daudi | Burkitt's lymphoma | CCL-213 | ATCC |
| L-428 | Hodgkin's lymphoma | Acc 197 | DSMZ |
| DU 145 | Prostate carcinoma | HTB-81 | ATCC |
| PC-3 | Prostate carcinoma | Acc 465 | DSMZ |
| MKN 1 | Gastric adenocarcinoma | 0252 | JCRB |
| KYSE 30 | Esophagus carcinoma | 0188 | JCRB |
| A549 | Lung carcinoma | CCL-185 | ATCC |
| HeLa | Cervix adenocarcinoma | CCL-2 | ATCC |
| C-33A | Cervix carcinoma | HTB-31 | ATCC |

*DSMZ: German National Resource Centre for Biological Material (Deutsche Sammlung von Mikroorganismen und Zellkulturen) Germany
ATCC: American Type Culture Collection, USA
JCRB: Japanese Collection of Research Bioresources-Cell Bank, Japan All cells used in anti-proliferative activity test were cultured at 37° C. in a humidified atmosphere containing 5% $CO_2$. Cells were grown according to the growth manual of each cell, in basal growth media, such as DMEM, MEM, F12K and1640 or 1640 plus F12 (all from Gibco BRL, US), supplemented with 5-20% heat-inactivated fetal bovine serum FBS, from Gibco BRL, US. The basal growth media for each individual cell line is listed in Table 2, below. All cell lines were examined daily in culture plates under an inverted microscope. Cells were harvested and used for experiments in their logarithmic growth phase with viabilities exceeding 90% as determined by trypan blue dye exclusion. The cell counts and viabilities were examined in standard hematocytometer.

TABLE 2

Culturing and Measuring Methods of Human Tumor Cell Lines

| Cell line | Culture media | Cells/Well | Measure methods |
|---|---|---|---|
| IGR-1 | DMEM | 5000 | crystal violet bioassay |
| IGR-37 | DMEM | 2000 | crystal violet bioassay |
| IPC-298 | 1640 | 2000 | crystal violet bioassay |
| HCT-8 | 1640 | 500 | crystal violet bioassay |
| LS 180 | MEM | 3000 | crystal violet bioassay |
| DLD-1 | 1640 | 1500 | crystal violet bioassay |
| Hep G2 | MEM | 1000 | crystal violet bioassay |
| Hep 3B | MEM | 800 | crystal violet bioassay |
| HuH-7 | DMEM | 4000 | crystal violet bioassay |
| PLC/PRF/5 | MEM | 6000 | crystal violet bioassay |
| KYSE 30 | 1640 + F12 | 1000 | crystal violet bioassay |
| DU 145 | MEM | 1000 | crystal violet bioassay |
| PC-3 | 1640 | 2000 | crystal violet bioassay |
| MKN 1 | 1640 | 2000 | crystal violet bioassay |
| A549 | F12K | 400 | crystal violet bioassay |
| SW 1116 | 1640 | 1000 | crystal violet bioassay |
| LS174T | MEM | 4000 | crystal violet bioassay |
| HeLa | MEM | 500 | crystal violet bioassay |
| C-33A | MEM | 1000 | crystal violet bioassay |
| A-375 | DMEM | 200 | crystal violet bioassay |
| HL 60(S) | 1640 | 800 | direct cell counting |
| Daudi | 1640 | 400 | direct cell counting |
| L-428 | 1640 | 800 | direct cell counting |

B. Procedure for Anti-Proliferative Assay

The cell lines with logarithmic growth phase were gently suspended in warmed (36° C.) media to a density of $2 \times 10^3$-$6 \times 10^4$ cells/ml (varying with cell line, see Table 2). 100 μl of cell suspension was seeded into each well of 96-well plate, followed by incubating for 6-8 hours at 37° C. Then equal volumes (100 μl) of Novaferon or HuIFN-α2b diluted in culture medium was added to the wells in triplicate. The plates were agitated gently for 4-5 seconds to mix the contents, and incubated at 37° C. for 6 days. The Novaferon and HuIFN-α2b samples were tested in the same plate in order to guarantee the comparability.

Two methods were used to determine the cell numbers in a cell well and to calculate the anti-proliferative activities of Novaferon and HuIFN-α2b according to the cell numbers.

A direct cell counting method was used to determine the cell number of suspension cell. After 6 days of culturing, suspension cell cultures were diluted with trypan blue (final concentration: 0.02%), and cell numbers were directly counted using hematocytometer.

Crystal violet bioassay method was used to determine the cell numbers of the adhesive cells (93). After 6 days of culturing, dead cells were removed by pipetting PBS up and down in the culture wells. Next, wells were filled with dye-fixer solution to stain the live cells for 1 hour. The dye-fixer solution contained 0.5% crystal violet, 5% formalin (V/V), 50% ethanol (V/V), and 0.85% NaCl in distilled water. Then microplates were rinsed copiously with tap water and allowed to dry. The stained cells were dissolved by 0.2 ml of 2-methoxyethanol. Optical density at 550 nm (OD550) (Model Opsys plate reader, Thermo Labsystems, US) was measured and used as the relative indicator of cell numbers.

The growth-inhibition rate was calculated by the following formula: inhibition rate %=$(1-(E-B)/(C-B)) \times 100$, where E was the number of cells or the value of $OD_{550}$ in Novaferon or HuIFN-α2b-treated wells at day 6; B was the number of cells or the value of $OD_{550}$ in a cell culture at day 0; C was the number of cells or the value of $OD_{550}$ in untreated wells at day 6.

The inhibition rate was expressed in conjunction with the compound concentrations. The $IC_{50}$ of Novaferon or HuIFN-α2b was estimated by using a range of sample concentrations. The data were fit to Sigmoidal curve (117) with Hill slope one: Y=min+(Max−min)/(1+10^($IC_{50}$ −X)) where X is the log concentrations of drug; Y is the inhibition rate; Min or Max is the minimum or maximum inhibition rate plateau. The $IC_{50}$ of various compounds against a particular target can be compared, where a lower $IC_{50}$ indicates a more potent compound.

The concentrations of Novaferon and HuIFN-α2b and the corresponding cell growth inhibition rates for Daudi cell line are presented in FIG. 4. Based on this data, the $IC_{50}$ of Novaferon and HuIFN-α2b to inhibit Daudi cell growth were calculated as 0.0174 pmol and 6.9550 pmol. Thus the $IC_{50}$ of Novaferon is about 1/400 of that of HuIFN-α2b, representing an approximately 400-fold increase of Novaferon's anti-proliferative potency in comparison to HuIFN-α2b.

The anti-proliferative activities of Novaferon were assessed and compared with those of HuIFN-α2b on 23 tumor cell lines, including 4 cell lines derived from melanoma (A-375, IGR-1, IGR-37, IPC-298), 5 colorectal adenocarcinoma cell lines (HCT-8, SW1116, LS 180, DLD-1, LS174T), 4 liver cancer cell lines (Hep G2, Hep 3B, HuH-7, PLC/PRF/5), 3 lymphoma cell lines (HL-60(S), Daudi, L-428), 2 prostate carcinoma cell lines (DU 145, PC-3), 2 cervical cancer cell lines (HeLa, C-33A), 1 gastric adenocarcinoma cell line (MKN 1), 1 lung carcinoma cell line (A 549) and one esophagus cancer cell line (KYSE 30). Novaferon exhibited much stronger anti-proliferative activities than those of HuIFN-α2b against all tested cancer cell lines. The extent of increase of the potency varied in the different cancer cell lines, and ranged from 16 to 1134 fold (Table 3, below).

TABLE 3

IC$_{50}$ values of Novaferon and HuIFN-α2b and the increased folds of tumor cell inhibition by Novaferon over HuIFN-α2b.

| Cell lines | IC$_{50}$ (pmol) HuIFN-α2b | Novaferon | Fold (Novaferon/HuIFN-α2b) |
|---|---|---|---|
| PLC/PRF/5 | 0.0407 | 0.0025 | 16 |
| A549 | 4.27 | 0.2202 | 19 |
| DU 145 | 0.1319 | 0.0036 | 36 |
| HepG2 | 0.1718 | 0.004 | 43 |
| HuH-7 | 0.1474 | 0.0026 | 58 |
| Hep3B | 4.3934 | 0.0758 | 58 |
| IPC-298 | 0.0516 | 0.0007 | 70 |
| LS174T | 0.0165 | 0.0002 | 74 |
| IGR-37 | 0.6017 | 0.0055 | 109 |
| PC-3 | 1.8777 | 0.0146 | 128 |
| HeLa | 0.2364 | 0.0017 | 141 |
| C-33A | 2.5242 | 0.0176 | 143 |
| MKN 1 | 0.233 | 0.0011 | 207 |
| HCT-8 | 2.9479 | 0.0139 | 212 |
| SW 1116 | 0.2278 | 0.001 | 222 |
| DLD-1 | 0.3977 | 0.0014 | 282 |
| HL-60(S) | 0.5855 | 0.0019 | 306 |
| LS 180 | 0.7579 | 0.0022 | 350 |
| Daudi | 6.955 | 0.0174 | 400 |
| KYSE 30 | 18.0134 | 0.0264 | 683 |
| A-375 | 1.4134 | 0.0019 | 733 |
| IGR-1 | 6.6718 | 0.0076 | 876 |
| L-428 | 17.2789 | 0.0152 | 1134 |

Example 8

In Vivo Tumor Model Experiments

A. Cell Culture and In Vivo Human Tumor Xenograft Models

Colon cancer cell line (LS 180), melanoma cell line (A-375) and liver cancer cell line (Hep G2) were obtained from the American Type Culture Collection (ATCC, Rockville, Md.). Prostate cancer cell line (PC-3) was obtained from German National Resource Centre for Biological Material (DSMZ, Deutsche Sammlung von Mikroorganismen and Zellkulturen, Germany). Lymphocytic cell line (HL 60(s)) was purchased from Japanese Collection of Research Biosources Cell Bank (JCRB, Japan). All cells were cultured according to their instructions (see Table 1). Briefly, LS 180 and Hep G2 were cultured in MEM medium. A-375 was cultured in DMEM. Both media were supplemented with 10% fetal bovine serum (FBS), 2 mM glutamine, 100 U/ml of penicillin, 100 mg/ml of streptomycin, 0.1 mM non-essential amino acids, and 1.0 mM sodium pyruvate. PC-3 and HL 60(S) cells were cultured in RPMI 1640, supplemented with 10% FBS, 100 U/ml of penicillin, and 100 mg/ml of streptomycin. All cells were maintained in 5% CO$_2$ atmosphere at 37° C.

Human cancer xenograft models were established using the methods described by Beverly et al (118). Log phase growing cancer cells were harvested from tissue culture plates, washed, and resuspended in phosphate-buffered saline (PBS, pH=7.5, 20 mM). Subcutaneous tumor xenografts were generated in 6-week-old athymic nude Balb/c mice by injecting 6×10$^6$ cells/0.3 ml (PC-3, HepG2), 4×10$^6$ cells/0.3 ml (LS 180), 2×10$^7$ cells/0.3 ml (HL 60(s)) or 8×10$^6$ cells/0.3 ml (A-375) subcutaneously on both sides in the flank region. For each in vivo tumor model, on day 6 after the tumor cell inoculation, tumor bearing mice (tumor volume is about 100 mm$^3$) were randomly divided into 7 or 8 groups with equal numbers of animals in each group, and treatment was commenced.

Novaferon and HuIFN-α2b were formulated with PBS solution. Daily subcutaneous injection of PBS alone, various doses of Novaferon, or HuIFN-α2b lasted for 30 days in total (PC-3, HepG2, A-375), 28 days (LS 180) or 21 days (HL 60(s)) from the day of grouping mice. For the treatment of 5-FU, 30 mg/kg of 5-FU was i.v. administrated once every two days for a total of 5 times. The groups and treatment doses are summarized below:

Group 1 (Control): PBS daily.
Group 2 (low dose of Novaferon): 1.25 μg/kg daily.
Group 3 (medium dose of Novaferon): 12.5 μg/kg daily.
Group 4 (high dose of Novaferon): 125 μg/kg daily.
Group 5 (low dose of HuIFN-α2b): 1.25 μg/kg daily.
Group 6 (medium dose of HuIFN-α2b): 12.5 μg/kg daily.
Group 7 (high dose of HuIFN-α2b): 125 μg/kg daily.
Group 8 (5-FU): 30 mg/kg, i.v. administration once every 2 days for 5 times.

Once treatment commenced, tumors were measured with a caliper once a week. The tumor volumes were calculated using the following formula: volume=0.5×(width)$^2$×(length). Mice were sacrificed at the day of treatment discontinuation (day 30 after commencement of the treatment). Solid tumors were isolated, photographed, and measured.

The growth inhibitory rate was calculated using the following formula: inhibitory rate=[1−T/C]×100%, where T is the average tumor weight in Novaferon-, HuIFN-α2b-, or 5-FU-treated groups; C is the average tumor weight in control group after treatment.

B. Human Prostate Cancer Xenograft Model

Figure 5:
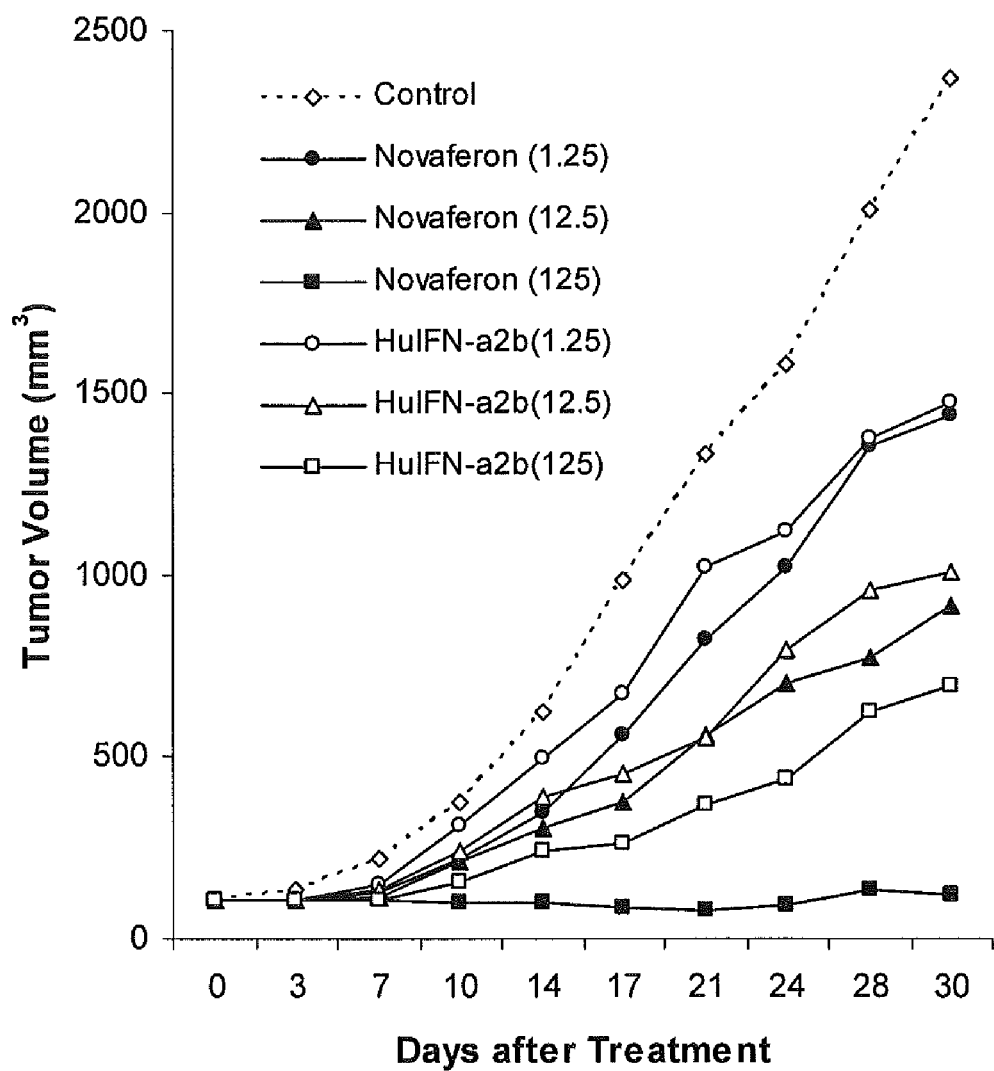
FIG. 5 is a graph showing the in vivo anti-tumor effects of Novaferon and HuIFN-α2b in nude mice with human prostate cancer PC-3 xenografts.

Prostate cancer PC-3 xenografts were treated with s.c. injection of 1.25, 12.5 or 125 μg/kg of Novaferon for 30 days. Novaferon exhibited strong, dose-dependent inhibition of the PC-3 tumor growth (P<0.05). As shown in FIG. 5 and Table 4, below, PC-3 tumor growth in Novaferon treated groups was greatly suppressed as compared with the control group of PBS treatment. For example, the average weight of PC-3 xenograft tumor mass in Novaferon-treated group (125 μg/kg), 0.091±0.081 g, was very significantly reduced as compared with control animals, 1.948±0.567 g (P<0.001) (Table 4). In other words, 30-day treatment of 125 μg/kg achieved 95.3% inhibition of the PC-3 tumor growth (Table 4).

TABLE 4

Tumor weight and growth inhibition rates of human prostate cancer PC-3 xenografts treated with Novaferon and HuIFN-α2b (n = 10)

| Group | Dose (μg/kg) | Tumor weight (g) (mean ± SD) | Inhibition rate(%) |
|---|---|---|---|
| Control | — | 1.948 ± 0.567 | — |
| Novaferon low dosage | 1.25 | 1.266 ± 0.457* | 35.0 |
| Novaferon medium dosage | 12.5 | 0.759 ± 0.574*** | 61.0 |
| Novaferon high dosage | 125 | 0.091 ± 0.081***@@@ | 95.3 |
| HuIFN-α2b low dosage | 1.25 | 1.284 ± 0.862 | 34.1 |
| HuIFN-α2b medium dosage | 12.5 | 0.790 ± 0.391*** | 59.4 |
| HuIFN-α2b high dosage | 125 | 0.476 ± 0.271*** | 75.6 | note:
*p < 0.05,
***p < 0.001: compared to control group;
@@@p < 0.001: compared to HuIFN-α2b high dose group Balb/c nude mice were treated with daily s.c. injection of Novaferon (1.25 µg/kg, 12.5 µg/kg or 125 µg/kg) for 30 days after 6×10⁶ live PC-3 cells were introduced subcutaneously into mice. Results were expressed as average tumor volume (mm³). FIG. 5 showed that all three doses of Novaferon exhibited dose-dependent inhibition of PC-3 tumor growth in comparison to the PBS control group (P<0.05). 125 µg/kg of Novaferon induced much stronger, or almost complete, inhibition of PC-3 tumor growth than that of HuIFN-α2b at the same dose (95.3% vs 75.6%, P<0.01) (Table 4).

It is interesting to notice that the longer treatment of Novaferon or HuIFN-α2b resulted in bigger differences in tumor growth inhibition in the high dose (125 µg/kg)-treated groups. The average volume of PC-3 tumor mass in the Novaferon-treated group was 107.9±68.7 mm³ versus 620.7±296.6 mm³ in HuIFN-α2b-treated group at day 28 (P<0.001) and 122.1±100.7 mm³ versus 691.9±428.3 mm³ at day 30 (P<0.001). This was also the case when the average tumor weight was considered after the termination of the observation (0.091±0.081 g in Novaferon high dosage group versus 0.476±0.271 gram in HuIFN-α2b high dosage group, P<0.001). This suggested that longer treatment of Novaferon at this dose may exhibit better or complete inhibition of PC-3 tumor growth in this xenograft model.

C. Human Liver Cancer Xenograft Model

The in vivo anti-tumor activity of Novaferon was also evaluated on liver cancer Hep G2 xenograft model. Novaferon exhibited effective, dose-dependent inhibition of Hep G2 tumor growth compared to control group (P<0.001). The average tumor volumes in Novaferon-treated groups (daily s.c. injection of 1.25, 12.5 or 125 µg/kg for 30 days) were 783.2±270.0, 459.3±414.3, and 104.6±56.5 mm³, respectively, in comparison with 2125.8±743.1 mm³ in PBS control group, 30-day treatment of 125 µg/kg of Novaferon achieved the highest inhibition of the Hep G2 (96.6%), which was significantly better than that by 125 µg/kg of HuIFN-α2b (89.2%, P<0.01). Longer treatment of Novaferon at this dose showed the trend of even better or complete inhibition. The average tumor weight at the end of observation period was 0.074±0.083 g in 125 µg/kg for the Novaferon-treated group, significantly less than that in 125 µg/kg of HuIFN-α2b-treated group (0.235±0.199 gram, P<0.001) (Table 5, below).

Figure 6:
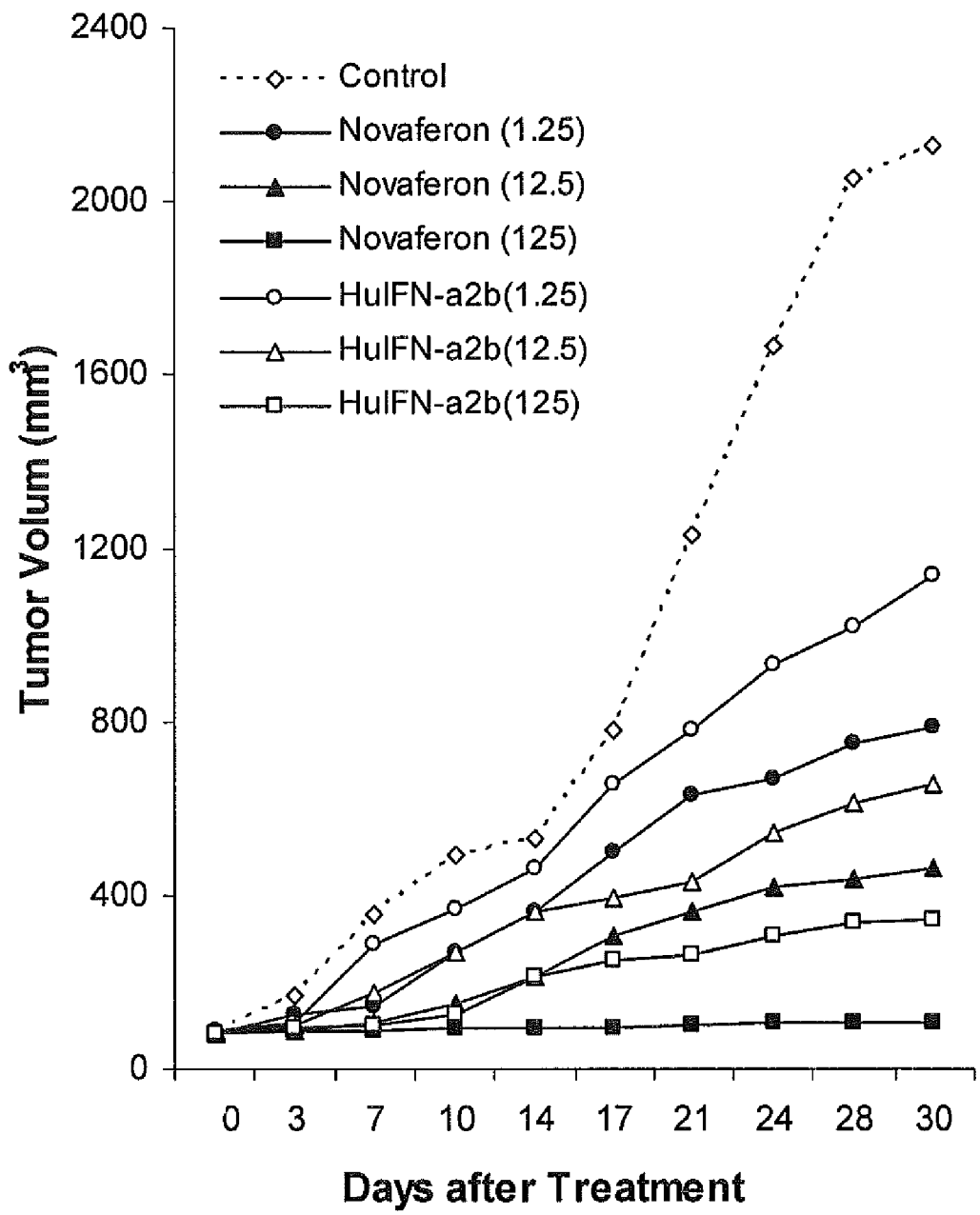
FIG. 6 is a graph showing the in vivo anti-tumor effects of Novaferon and HuIFN-α2b in nude mice with human liver cancer Hep G2 xenografts.

Balb/c nude mice were treated with daily s.c. injection of Novaferon (1.25 µg/kg, 12.5 µg/kg and 125 µg/kg) for 30 days after 6×10⁶ live Hep G2 cells were introduced subcutaneously into mice. Results were expressed as average tumor volume (mm³). FIG. 6 showed that all three doses of Novaferon exhibited dose-dependent inhibition of Hep G2 tumor growth in comparison to the PBS control group (P<0.001). 125 µg/kg of Novaferon induced much stronger, or almost complete, inhibition of Hep G2 tumor growth than that of HuIFN-α2b at the same dose (96.6% vs 89.2%, P<0.05) (Table 5).

TABLE 5

Tumor weight and growth inhibition rates of human liver cancer cell Hep G2 xenografts treated with Novaferon and HuIFN-α2b (n = 10)

| Group | Dose (µg/kg) | Tumor weight (g) (Mean ± SD) | Inhibition rate(%) |
|---|---|---|---|
| Control | — | 2.179 ± 0.578 | — |
| Novaferon low dosage | 1.25 | 0.797 ± 0.397*** | 63.4 |

TABLE 5-continued

Tumor weight and growth inhibition rates of human liver cancer cell Hep G2 xenografts treated with Novaferon and HuIFN-α2b (n = 10)

| Group | Dose (µg/kg) | Tumor weight (g) (Mean ± SD) | Inhibition rate(%) |
|---|---|---|---|
| Novaferon medium dosage | 12.5 | 0.321 ± 0.300*** | 85.3 |
| Novaferon high dosage | 125 | 0.074 ± 0.083***@ | 96.6 |
| HuIFN-α2b low dosage | 1.25 | 1.070 ± 0.587** | 50.9 |
| HuIFN-α2b medium dosage | 12.5 | 0.531 ± 0.287*** | 75.6 |
| HuIFN-α2b high dosage | 125 | 0.235 ± 0.199*** | 89.2 |

Note:
**p < 0.01,
***p < 0.001, compared to control group.
@p < 0.01, compared with HuIFN-α2b high dosage group D. Human Melanoma Xenograft Model The in vivo anti-tumor activity of Novaferon was further evaluated in malignant melanoma A-375 xenograft model. A-375 cell line (ATCC number: CRL-1619) was derived from a human malignant solid tumor. Novaferon exhibited effective, dose-dependent inhibition of A-375 tumor growth compared to control group (P<0.001). The inhibition rates in the Novaferon-treated groups (daily s.c. injection of 1.25, 12.5 or 125 µg/kg for 28 days) were 40.1%, 75.0% and 82.8% respectively, in comparison with PBS control group (P<0.001) (Table 6, below). 30-day treatment of 125 µg/kg of Novaferon achieved the highest inhibition of the A-375 (82.8%), which was significantly better than that by 125 µg/kg of HuIFN-α2b (69.9%, P<0.001).

Interestingly, Novaferon exhibited more effective inhibition of the growth of melanoma cell A-375 than the chemotherapeutic agent, 5-FU (Table 6). On day 30, for instance, the mean tumor weights of in the groups treated with 12.5 µg/kg or 125 µg/kg of Novaferon were 0.763±0.187 (P<0.01) and 0.527±0.149 (P<0.001) grams, whereas the mean tumor weight for the group treated with 5-FU, 30 mg/kg, was 1.004±0.105 gram (Table 6). This indicates that Novaferon may be more effective for the treatment of human melanoma A-375 than 5-FU.

Figure 7:
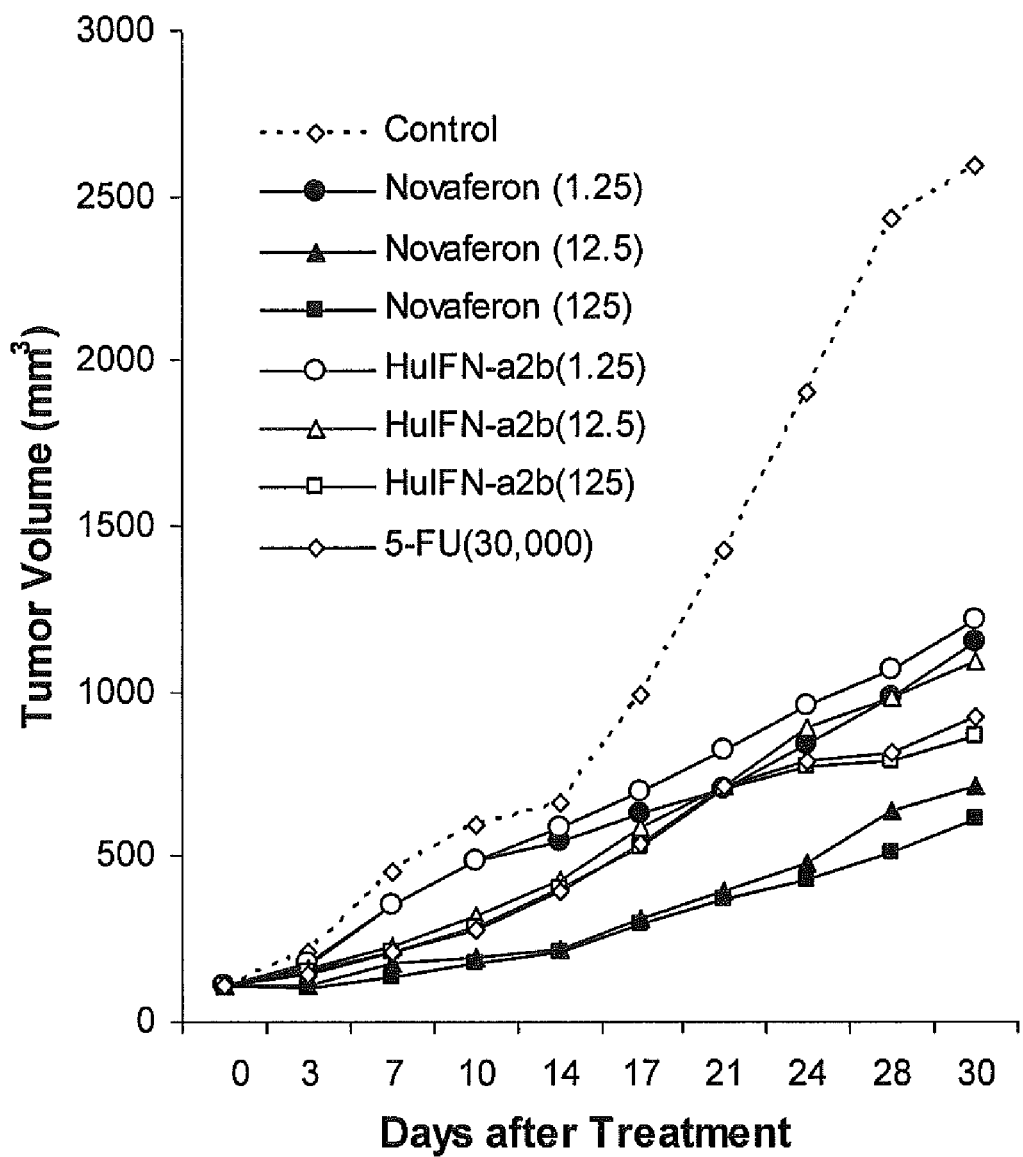
FIG. 7 is a graph showing the in vivo anti-tumor effects of Novaferon and HuIFN-α2b in nude mice with human melanoma A-375 xenografts.

Balb/c nude mice were treated with the daily s.c. injection of Novaferon (1.25 µg/kg, 12.5 µg/kg and 125 µg/kg) for 28 days after 8×10⁶ A-375 cells were introduced subcutaneously into mice. Results are expressed as average tumor volume (mm³). FIG. 7 showed that all three doses of Novaferon exhibited dose-dependent inhibition of A-375 tumor growth in comparison to the PBS control group (P<0.001). 125 µg/kg of Novaferon induced stronger inhibition of A-375 tumor growth than that by HuIFN-α2b at the same dose (82.8% vs 69.9%, P<0.001) (FIG. 7). Both 12.5 µg/kg and 125 µg/kg of Novaferon showed better suppression (75.0% and 82.8% respectively) of the tumor growth than by 5-FU (67.2%, P<0.01 and P<0.001) (FIG. 7).

TABLE 6

Tumor weight and growth inhibition rates of human melanoma cell A-375 xenografts treated with Novaferon and HuIFN-α2b (n = 10)

| Group | Dose (μg/kg) | Tumor weight (g) (X ± SD) | Inhibition rate (%) |
|---|---|---|---|
| Control | — | 3.057 ± 0.384 | — |
| Novaferon low dosage | 1.25 | 1.830 ± 0.289*** | 40.1 |
| Novaferon medium | 12.5 | 0.763 ± 0.187***&&$$$ | 75.0 |
| Novaferon high dosage | 125 | 0.527 ± 0.149***&&&@@@ | 82.8 |
| HuIFN-α2b low dosage | 1.25 | 1.890 ± 0.148*** | 38.2 |
| HuIFN-α2b medium | 12.5 | 1.681 ± 0.132*** | 45.0 |
| HuIFN-α2b high dosage | 125 | 0.920 ± 0.139*** | 69.9 |
| 5-FU | 30,000 | 1.004 ± 0.105*** | 67.2 | note:
***p < 0.001, compared to control group;
$$$p < 0.001, compared to HuIFN-α2b medium dosage (12.5);
@@@p < 0.001 compared to HuIFN-α2b high dosage (125) group;
&&p < 0.01,
&&&p < 0.001, compared to 5-FU group E. Human Colon Cancer Xenograft Model The in vivo anti-tumor activity of Novaferon was evaluated in colon cancer LS 180 xenograft model. LS 180 cell line (ATCC number: CL-187) was derived from a human colon adenocarcinoma. Novaferon exhibited effective, dose-dependent inhibition of colon cancer LS180 tumor growth compared to control group (P<0.001). The inhibition rates in the Novaferon-treated groups (daily s.c. injection of 1.25, 12.5 or 125 μg/kg for 28 days) were 75.0%, 80.5% and 92.5% respectively compared to the PBS control group (P<0.001, Table 7, below). 28-day treatment of 125 μg/kg of Novaferon achieved the highest inhibition of LS 180 tumor growth (92.5%), which was significantly better than that by 125 μg/kg of HuIFN-α2b (82.3%, P<0.001).

Following 28-day treatment, 12.5 μg/kg of Novaferon inhibited the growth of LS 180 cancer xenografts similarly to 5-FU (30 mg/kg) in terms of the average tumor weights, animal model indicates that Novaferon has the potential to work as a very effective anti-colon cancer agent in a clinical setting.

Figure 8:
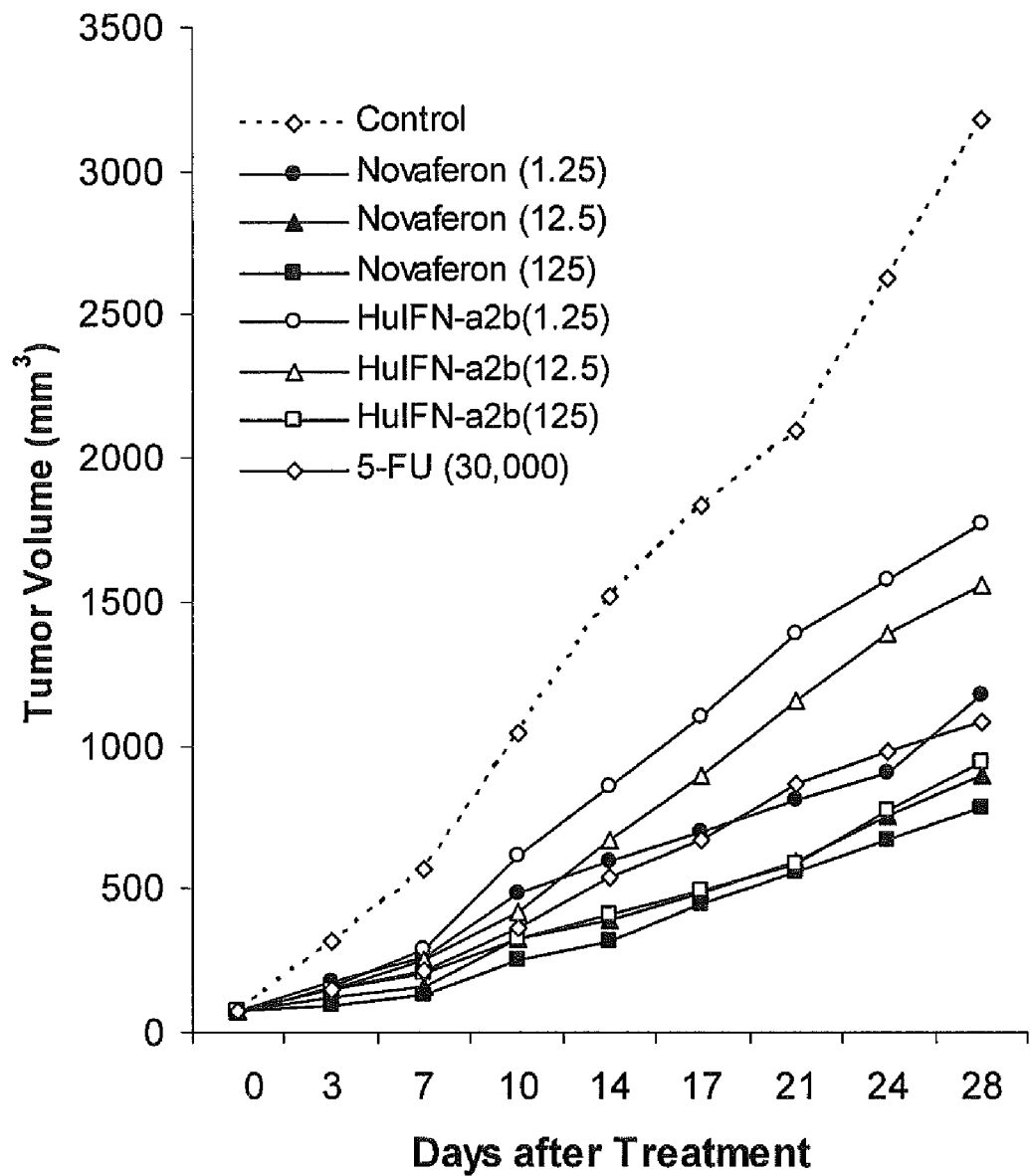
FIG. 8 is a graph showing the in vivo anti-tumor effects of Novaferon and HuIFN-α2b in nude mice with colon cancer LS 180 xenografts.

Balb/c nude mice were treated with a daily injection of Novaferon (1.25 μg/kg, 12.5 μg/kg and 125 μg/kg) for 28 days after 4×10⁶ 1 LS 180 cells were introduced subcutaneously into mice. Results were expressed as average tumor volume (mm³). FIG. 8 showed that all three doses of Novaferon exhibited dose-dependent inhibition of LS 180 tumor growth in comparison to the PBS control group (P<0.001). 125 μg/kg of Novaferon induced stronger inhibition of LS 180 tumor growth than that by HuIFN-α2b at the same dose (92.5% vs 82.3%, P<0.001) (Table 7). Both 1.25 μg/kg and 12.5 μg/kg of Novaferon achieved similar suppression (75.0% and 80.5% respectively) of the tumor growth in comparison to 5-FU (81.8%) (Table 7, FIG. 8). However, 125 g μg/kg of Novaferon exhibited much better inhibition of LS 180 tumor growth than that by 5-FU (92.5% vs 81.8%, P<0.001).

TABLE 7

Tumor weight and growth inhibition rates of human colon cancer cell LS 180 xenografts treated with Novaferon and HuIFN-α2b (n = 10)

| Group | Dose (μg/kg) | Tumor weight (g) (X ± SD) | Inhibition rate (%) |
|---|---|---|---|
| Control | — | 4.170 ± 3.409 | — |
| Novaferon low dosage | 1.25 | 1.043 ± 0.433*** | 75.0 |
| Novaferon medium dosage | 12.5 | 0.815 ± 0.221*** | 80.5 |
| Novaferon high dosage | 125 | 0.314 ± 0.086***&&&@@@ | 92.5 |
| HuIFN-α2b low dosage | 1.25 | 1.225 ± 0.565*** | 70.6 |
| HuIFN-α2b medium | 12.5 | 1.076 ± 0.442*** | 74.2 |
| HuIFN-α2b high dosage | 125 | 0.740 ± 0.310*** | 82.3 |
| 5-FU | 30,000 | 0.758 ± 0.227*** | 81.8 |

Note:
***p < 0.001, compared to control group;
@@@p < 0.001, compare to HuIFN-α2b high dosage;
&&&p < 0.001, compare to 5-FU group (0.815±0.221 grams vs 0.758±0.227 grams). 125 μg/kg of Novaferon inhibited the tumor growth of LS 180 significantly better than 30 mg/kg of 5-FU, (92.5% vs 81.8%, P<0.001) (Table 7 and FIG. 8). These observation was extremely interesting, considering the routine clinical application of 5-FU in the standard chemotherapy to patients with colon cancer. The better suppression by Novaferon of LS 180 tumor growth in F. Human Leukemia Xenograft Model The in vivo anti-tumor activity of Novaferon was also assessed in HL 60(s) lymphocytic leukemia xenograft model. Novaferon exhibited effective, dose-dependent inhibition of HL 60(s) tumor growth compared to control group (P<0.001). The inhibition rates in the Novaferon-treated groups (daily s.c. injection of 1.25, 12.5 or 125 μg/kg for 28 days) were 43.8%, 55.2% and 80.4% respectively compared to the PBS control group (P<0.001, Table 8, below). 21-day treatment of 125 μg/kg of Novaferon achieved the highest inhibition of HL 60(s) tumor growth (80.4%), which was significantly better than that by 125 μg/kg of HuIFN-α2b (69.8%, P<0.05).

Figure 9:
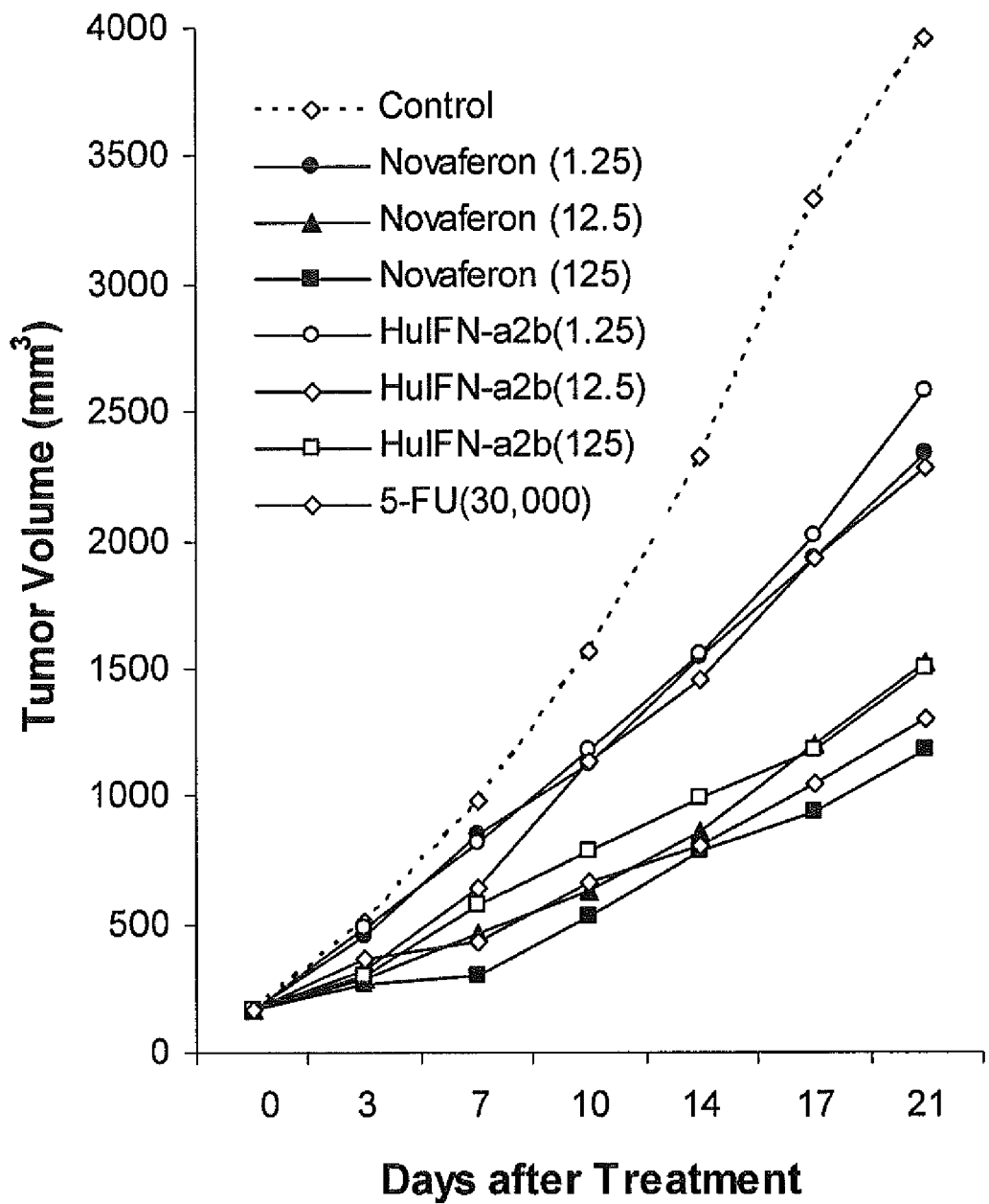
FIG. 9 is a graph showing the in vivo anti-tumor effects of Novaferon and HuIFN-α2b in nude mice with human leukemia HL 60(S) xenografts.

Balb/c mice were treated with the daily s.c. injection of Novaferon (1.25 μg/kg, 12.5 μg/kg and 125 μg/kg) for 21 days after $2\times10^7$ live HL 60(s) cells were introduced subcutaneously into mice. Results were expressed as average tumor volume ($mm^3$). FIG. 9 showed that all three doses of Novaferon exhibited dose-dependent inhibition of LS180 tumor growth in comparison to the PBS control group (P<0.001). 125 μg/kg of Novaferon induced stronger inhibition of LS 180 tumor growth than that by HuIFN-α2b at the same dose (80.4% vs 69.8%, P<0.05), and similar inhibition comparing to 5-FU (FIG. 9, Table 8).

TABLE 8

Tumor weight and growth inhibition rates of human leukemia Cell LS 60(S) xenografts treated with Novaferon and HuIFN-α2b (n = 10)

| Group | Dose (μg/kg) | Tumor weight (g) (X ± SD) | Inhibition rate (%) |
|---|---|---|---|
| Control | — | 3.723 ± 0.750 | — |
| Novaferon low dosage | 1.25 | 2.091 ± 0.653*** | 43.8 |
| Novaferon medium dosage | 12.5 | 1.668 ± 0.665*** | 55.2 |
| Novaferon high dosage | 125 | 0.729 ± 0.332***@ | 80.4 |
| HuIFN-α2b low dosage | 1.25 | 2.401 ± 0.698*** | 35.5 |
| HuIFN-α2b medium dosage | 12.5 | 1.870 ± 0.660*** | 49.8 |
| HuIFN-α2b high dosage | 125 | 1.124 ± 0.397*** | 69.8 |
| 5-FU | 30,000 | 0.893 ± 0.289*** | 76.0 |

Note:
***p < 0.001, compared to control group;
@p < 0.05, compared to HuIFN-α2b high dosage (125) group G. General Condition of the Mice during Novaferon Treatment The mice with the various xenografts of human cancers were closely observed during the period of Novaferon, HuIFN-α2b or 5-FU treatment. Unlike in the 5-Fu-treated groups, mice in all Novaferon- or HuIFN-α2b-treated groups generally ate and behaved normally, and had no weight loss. The 5-FU-treated nice showed typical changes of eating and behavior, and weight loss. These observations indicate that while showing similar or better anti-cancer potency than 5-FU in the xenograft animal models, Novaferon may be more specific toward the inhibition of cancer cell and have much less effects on normal cells and/or physiological functions. These may be translated into a better tolerance and superior therapeutic effects in human applications.

As will be apparent to those skilled in the art in the light of the foregoing disclosure, many alterations and modifications are possible in the practice of the invention without departing from the spirit or scope thereof. Accordingly, the scope of the invention is to be construed in accordance with the substance defined by the appended claims.

REFERENCES

1. Interferon nomenclature. Nature. 1980; 286 (5769):110
2. Isaacs A and Lindenmann J. Production of virial interfering substance. U.S. Pat. No. 369,922. Oct. 17, 1972
3. Jonasch E and Haluska F G. Interferon in oncological practice: review of interferon biology, clinical applications, and toxicities. Oncologist. 2001; 6(1):34-55
4. Lengyel P. Biochemistry of interferons and their actions. Annu Rev Biochem. 1982; 51:251-282
5. Gresser I and Tovey M G. Antitumor effects of interferon. Biochim Biophys Acta. 1978; 516(2):231-247
6. Samuel C E. Antiviral actions of interferons. Clin Microbiol Rev. 2001; 14(4):778-809
7. Theofilopoulos A N, et al. Type I interferons (alpha/beta) in immunity and autoimmunity. Annu Rev Immunol. 2005; 23:307-336
8. Uze G, et al. Alpha and beta interferons and their receptor and their friends and relations. J Interferon Cytokine Res. 1995; 15(1):3-26
9. Knight E Jr. Interferon: purification and initial characterization from human diploid cells. Proc Natl Acad Sci USA. 1976; 73(2):520-523
10. Pestka S, et al. Interferons, interferon-like cytokines, and their receptors. Immunol Rev. 2004; 202:8-32
11. Horisberger M A and Di Marco S. Interferon-alpha hybrids. Pharmacol Ther. 1995; 66(3):507-534
12. Horton H M, et al. Antitumor effects of interferon-omega: in vivo therapy of human tumor xenografts in nude mice. Cancer Res. 1999; 59(16):4064-4068
13. Hardy M P, et al. Characterization of the type I interferon locus and identification of novel genes. Genomics.2004; 84(2):331-345.
14. Chen J. et al. Human interferon-ε: a type I interferon. U.S. Pat. No. 6,569,420. May 27, 2003
15. Pestka S, et al. Interleukin-10 and releated cytokines and receptors. Annu Rev Immunol 2004, 22:929-979
16. Nardelli B, et al. Regulatory effect of IFN-kappa, a novel type I IFN, on cytokine production by cells of the innate immune system. J. Immunol. 2002; 169(9):4822-4830
17. LaFleur D W, et al. Interferon-kappa, a novel type I interferon expressed in human keratinocytes. J Biol Chem. 2001; 276(43):39765-39771
18. Subramaniam P S, Johnson H M. The IFNAR1 subunit of the type I IFN receptor complex contains a functional nuclear localization sequence. FEBS Lett. 2004; 578(3): 207-210
19. Goodbourn S, et al. Interferons: cell signalling, immune modulation, antiviral response and virus countermeasures. J Gen Virol. 2000; 81(Pt 10):2341-2364
20. Wang K, et al. Inhibition of neutrophil apoptosis by type 1 IFN depends on cross-talk between phosphoinositol 3-kinase, protein kinase C-delta, and NF-kappa B signaling pathways. J Immunol. 2003; 171(2):1035-1041
21. Katze M G. Interferon, PKR, virology, and genomics: what is past and what is next in the new millennium? J Interferon Cytokine Res. 2002; 22(3):283-286
22. Chawla-Sarkar M, et al. Apoptosis and interferons: role of interferon-stimulated genes as mediators of apoptosis. Apoptosis. 2003; 8(3):237-249
23. Kirkwood J. Cancer immunotherapy: the interferon-alpha experience. Semin Oncol. 2002; 29(3 Suppl 7):18-26
24. Hofmann V, et al. Hairy cell leukemia: an interferon deficient disease? Cancer Treat Rev. 1985; Suppl B: 33-37
25. Stone R M, et al. Recombinant human gamma interferon administered by continuous intravenous infusion in acute myelogenous leukemia and myelodysplastic syndromes. Am J Clin Oncol. 1993; 16(2):159-163
26. Talpaz M, et al. Human leukocyte interferon to control thrombocytosis in chronic myelogenous leukemia. Ann Intern Med. 1983; 99(6):789-792
27. Talpaz M, et al. Changes in granulocyte-monocyte colony-forming cells among leukocyte-interferon-treated chronic myelogenous leukemia patients. Exp Hematol. 1986; 14(7):668-671

28. Strander H, et al. Long-term adjuvant interferon treatment of human osteosarcoma. A pilot study. Acta Oncol. 1995; 34(6):877-880
29. Dogan B, et al. Intralesional alfa-2a interferon therapy for basal cell carcinoma. Cancer Lett. 1995; 91(2):215-219
30. Fetell M R, et al. Intratumor administration of beta-interferon in recurrent malignant gliomas. A phase I clinical and laboratory study. Cancer. 1990; 65(1):78-83
31. Muss H B. The use of interferon in renal cell carcinoma. Eur J Cancer. 1991; 27 (Suppl 4):S84-87
32. Peest D, et al. Cytokine therapy in multiple myeloma. Br. J Haematol. 1996; 94(3):425-432
33. Ikic D, et al. Local interferon therapy for melanoma patients. Int. J Dermatol. 1995; 34(12):872-874
34. Rybak M E, et al. Interferon therapy of relapsed and refractory Hodgkin's disease: Cancer and Leukemia Group B Study 8652. J Biol. Response Mod. 1990; 9(1): 1-4
35. Kaufmann R, et al. Temozolomide in combination with interferon-alpha versus temozolomide alone in patients with advanced metastatic melanoma: a randomized, phase III, multicenter study from the Dermatologic Cooperative Oncology Group. J Clin Oncol. 2005; 23(35):9001-9007
36. Lane H C. The role of alpha-interferon in patients with human immunodeficiency virus infection. Semin Oncol. 1991; 18(Suppl 7):46-52
37. Woo M H and Brunakis T G. Interferon alfa in the treatment of chronic viral hepatitis B and C. Ann. Pharmacother. 1997; 31(3):330-337
38. Gibas A L. Use of interferon in the treatment of chronic viral hepatitis. Gastroenterologist. 1993; 1(2):129-142
39. Levine L A, et al. Treatment of subclinical intraurethral human papilloma virus infection with interferon alfa-2b. Urology. 1996; 47(4):553-557
40. Ho M. Interferon for the treatment of infections. Annu Rev Med. 1987; 38:51-59
41. Wintergerst U and Belohradsky B H. Acyclovir monotherapy versus acyclovir plus beta-interferon in focal viral encephalitis in children. Infection. 1992; 20(4):207-212
42. Bogdan C, et al. The role of type I interferons in non-viral infections. Immunol Rev. 2004; 202:33-48
43. Condos R, et al. Treatment of multidrug-resistant pulmonary tuberculosis with interferon-gamma via aerosol. Lancet. 1997; 349(9064):1513-1515
44. Giosue S, et al. Aerosolized interferon-alpha treatment in patients with multi-drug-resistant pulmonary tuberculosis. Eur Cytokine Netw. 2000; 11(1):99-104
45. Raad I, et al. Use of adjunctive treatment with interferon-gamma in an immunocompromised patient who had refractory multidrug-resistant tuberculosis of the brain. Clin Infect Dis. 1996; 22:572-574
46. Fernandez O, et al. Treatment of relapsing-remitting multiple sclerosis with natural interferon beta: a multicenter, randomized clinical trial. Mult. Seler. 1995; Suppl 1:S67-69;
47. Freedman M S, et al. Randomized study of once-weekly interferon beta-la therapy in relapsing multiple sclerosis: three-year data from the OWIMS study. Mult Scler. 2005; 11(1):41-45
48. Shiozawa S, et al. Single-blinded controlled trial of low-dose oral IFN-alpha for the treatment of xerostomia in patients with Sjogren's syndrome. J Interferon Cytokine Res. 1998; 18(4):255-262
49. Wandinger K P, et al. Diminished production of type-I interferons and interleukin-2 in patients with multiple sclerosis. J Neurol Sci. 1997; 149(1):87-93
50. Steegmann J L, et al. Interferon alpha for chronic myeloid leukemia relapsing after allogeneic bone marrow transplantation. Bone Marrow Transplant. 1999; 23(5):483-488
51. Kirkwood J M, et al. High dose Interferon alfa 2b significantly prolongs relapse free survival compared with GM2-KLH/QS-21 vaccine in patients with resected stage IIB-III melanoma: Results of Intergroup Trial E1694/S9512/C509081. J Clin Oncol 2001; 19:2370-2380
52. Bonnem E M. alpha Interferon: the potential drug of adjuvant therapy: past achievements and future challenges. Eur J Cancer. 1991; 27 Suppl 4:S2-6
53. Folkman J. Successful treatment of an angiogenic disease. N Engl J Med. 1989; 320:1211-1212
54. Clifford J L, et al. Retinoids and interferons as antiangiogenic cancer drugs. In: Teicher B A, ed. Antiangiogenic Agents in Cancer Therapy. Totowa, N.J.: Humana Press Inc; 1999; 355-370
55. Kaban L B, et al. Antiangiogenic therapy of a recurrent giant cell tumor of the mandible with interferon alfa-2a. Pediatrics. 1999; 103:1145-1149
56. Sleijfer S, et al. Side effects of interferon-alpha therapy. Pharm World Sci. 2005; 27(6):423-431
57. Bell L, et al. Structure and properties of modified Interferons. U.S. Pat. No. 4,914,033. Apr. 3, 1990
58. Meyer F, et al. Hybrid Interferons. U.S. Pat. No. 5,071,761. Dec. 10, 1991
59. Streuli M, et al. Target cell specificity of two species derived from them. Proc Natl Acad Sci USA. 1981; 78(5): 2848-2852
60. Zoon K, et al. interferon alpha hybrids. U.S. Pat. No. 6,685,933. Feb. 3, 2004
61. Gangemi J D. Antiviral combination, and method of treatment. U.S. Pat. No. 5,137,720 Aug. 11, 1992
62. Johnson H M, et al. Hybrid interferon tau/type I interferon polypeptides U.S. Pat. No. 6,174,996. Jan. 16, 2001
63. Raj, N B, et al. Synthesis, antiviral activity, and conformational characterization of mouse-human a-interferon hybrids. J Biol Chem. 1988; 263(18):8943-8952
64. Mark D F, et al. Site-specific mutagenesis of the human fibroblast interferon gene. Proc Natl Acad Sci USA 1984; 81(18): 5662-5666
65. Bentzien J, et al. Recombinant interferon-beta mutants. U.S. Pat. No. 6,514,729. Feb. 4, 2003
66. Stemmer W P C. Methods for in vitro recombination. U.S. Pat. No. 5,605,793. Feb. 25, 1997
67. Chang C C, et al. Evolution of a cytokine using DNA family shuffling. Nat Biotechnol. 1999; 17(8):793-797
68. Blatt L M, et al. The biologic activity and molecular characterization of a novel synthetic interferon-alpha species, consensus interferon. J interferon cytokine Res. 1996; 16:489-499
69. Tatusova T A and Madden T L. BLAST 2 Sequences, a new tool for comparing protein and nucleotide sequences. FEMS Microbiol Lett. 1999; 174(2): 247-250
70. Bowie J U, et al. Deciphering the Message in Protein Sequences: Tolerance to Amino acid Substitutions. Science 1990; 247(4948):1306-1310
71. Creighton T E. Posttranslational covalent modification of polypeptide chains. In Proteins: Structure and Molecular Properties. Ed by Creighton T E. W. H. Freeman & Co. 1993; pp. 78-99. San Francisco, US
72. Aplin J D and Wriston J C Jr. Preparation, properties, and applications of carbohydrate conjugates of proteins and lipids. CRC Crit Rev Biochem. 1981; 10(4):259-306
73. Edge A S, et al. Deglycosylation of glycoproteins by trifluoromethanesulfonic acid. Anal Biochem. 1981; 118 (1):131-137

74. Thotakura N P and Bohl O P. Enzymatic deglycosylation of glycoproteins. Meth Enzymol.1987; 138:350-359
75. Peck G E, et al. Pharmaceutical manufacturing. In Remington: The Science and Practice of Pharmacy, 21$^{st}$ ed. Edited by University of the Sciences in Philadelphia (USIP), Lippincott Williams and Wilkins. 2006, page: 691-1094. Pennsylvania, US
76. Shimizu K, et al. Plasminogen activator derivatives U.S. Pat. No. 4,640,835. Feb. 3, 1987
77. Mitra G. Covalently attached complex of alpha-1-proteinase inhibitor with a water soluble polymer. U.S. Pat. No. 4,496,689. Jan. 29, 1985
78. Nakagawa Y, et al. Chemically modified protein with polyethyleneglycol U.S. Pat. No. 4,791,192. Dec. 13, 1988
79. Davis F, et al. Non-immunogenic polypeptides U.S. Pat. No. 4,179,337. Dec. 18, 1979
80. Field J, et al. Purification of a RAS-responsive adenylyl cyclase complex from Saccharomyces cerevisiae by use of an epitope addition method. Mol Cell Biol. 1988; 8(5): 215921-2165
81. Evan G I, et al. Isolation of monoclonal antibodies specific for human c-myc proto-oncogene product. Mol Cell Biol. 1985; 5(12):3610-3616
82. Paborsky L R, et al. Mammalian cell transient expression of tissue factor for the production of antigen. Protein Eng. 1990; 3(6):547-553
83. Einhauer A and Jungbauer A. The FLAG peptide, a versatile fusion tag for the purification of recombinant proteins. J Biochem Biophys Methods. 2001; 49(1-3):455-465
84. Skinner H, et al. Use of the Glu-Glu-Phe C-terminal epitope for rapid purification of the catalytic domain of normal and mutant ras GTPase-activating proteins. J Biol Chem. 1991; 266(22):14163-14166
85. Lutz-Freyermuth C, et al. Quantitative determination that one of two potential RNA-binding domains of the A protein component of the U1 small nuclear ribonucleoprotein complex binds with high affinity to stem-loop II of U1 RNA. Proc Natl Acad Sci USA. 1990; 87(16):6393-6397
86. Zhang Z Q, et al. Construction and application of a high level expression vector containing $P_R P_L$ promoter. Chinese J of Virol. 1990; 2:18-23
87. Kingston R E, et al. Introduction of DNA into mammalian cells. In Current Protocols In Molecular Biology edited by Ausubel F M, et al. 2003; page: 9.0.1-9.15.20, Jhn Wiley & Sons, Inc. US
88. McNeill T A. Interferon assay. J Immunol Methods. 1981; 46(2):121-127
89. Rubinstein S, et al. Convenient assay for interferon. 1. Viral. 1981; 37: 755-758
90. Horisberger M A and de Staritzky K. A recombinant human interferon-α B/D hybrid with a broad hostrange. J Gen Virol. 1987; 68:945-948
91. Stitz L and Schellekens H. Influence of input multiplicity of infection on the antiviral activity of interferon. J Gen Virol. 1980; 46:205-210
92. Yeo E Y, et al. Effect of short-term ethanol on the proliferative response of Swiss 3T3 cells to mitogenic growth factors, Exp Mol Med. 2000: 32: 161-169
93. Vignesh R C, et al. Effect of ethanol on human osteosarcoma cell proliferation, differentiation and mineralization. Toxicology. 2006; 220(1):63-70
94. Cavanaugh P F Jr, et al. A semi-automated neutral red based chemosensitivity assay for drug screening. Investigational New Drugs. 1990; 8(4):347-354
95. Raines E W and Ross R. Purification of human platelet-derived growth factor. Methods Enzymol. 1985; 109:749-773
96. Wahl A F, et al. Gene expression of human DNA polymerase alpha during cell proliferation and the cell cycle. Mol Cell Biol. 1988; 8(11):5016-5025
97. Cook J A and Mitchel J B. Viability measurements in mammalian cell systems. Anal Biochem. 1989; 179(1):1-7
98. Porstmann T, et al. Quantitation of 5-bromo-2-deoxyuridine incorporation into DNA: an enzyme immunoassay for the assessment of the lymphoid cell proliferative response. J Immunol Methods. 1985; 82(1):169-179
99. Mosmann T. Rapid colorimetric assay for cellular growth and survival: application to proliferation and cytotoxicity assays. J Immunol Methods. 1983; 65(1-2):55-63
100. Scudiero D A, et al. Evaluation of a soluble tetrazolium/formazan assay for cell growth and drug sensitivity in culture using human and other tumor cell lines. Cancer Res. 1988; 48(17):4827-4833
101. Evinger M And Pestka S. Assay of growth inhibition in lymphoblastoid cell cultures. Methods Enzymol. 1981; 79(Pt B):362-368
102. Meister A, et al. Biological activities and receptor binding of two human recombinant interferons and their hybrids. J Gen Virol. 1986; 67(Pt 8):1633-43
103. Frincke J, et al. Interferon antibody compositions having an extended serum half-life. U.S. Pat. No. 5,055,289. Oct. 8, 1991
104. Chang T and Yu L. Hybrid with interferon-beta, and an immunoglobulin Fe joined by a peptide linker. U.S. Pat. No. 5,908,626. Jun. 1, 1999
105. Nieforth K A, et al. Use of an indirect pharmacodynamic stimulation model of MX protein induction to compare in vivo activity of interferon alfa-2a and a polyethylene glycol-modified derivative in healthy subjects. Clin Pharmacol Ther. 1996; 59(6):636-646
106. Ekwuribe N N. Conjugation-stabilized therapeutic agent compositions, delivery and diagnostic formulations comprising same, and method of making and using the same. U.S. Pat. No. 5,681,811. Oct. 28, 1997
107. Gilbert C W and Cho M-O. Interferon polymer conjugates. U.S. Pat. No. 5,711,944. Jan. 27, 1998
108. Greenwald R and Gilbert C W. Interferon polymer conjugates and process for preparing the same. U.S. Pat. No. 5,738,846. Apr. 14, 1998
109. Letsinger R L, et al. Cholesteryl-conjugated oligonucleotides: synthesis, properties, and activity as inhibitors of replication of human immunodeficiency virus in cell culture. Proc Natl Acad Sci USA. 1989; 86(17): 6553-6556
110. Brower V. Naked DNA vaccines come of age. Nat Biotechnol. 1998; 16(13):1304-1305
111. Coen D M. The polymerase chain reaction. In Current Protocols in Molecular Biology. Edited by Ausubel F M. 2001, page: 15.01-15.7.8. Jhn Wiley & Sons, Inc. US
112. Stemmer W P. DNA shuffling by random fragmentation and reassembly: in vitro recombination for molecular evolution. Proc Natl Acad Sci USA. 1994; 91(22): 10747-10751
113. Armstrong J A. Cytopathic effect inhibition assay for interferon: microculture plate assay. Methods Enzymol. 1981; 78(pt A): 381-387
114. Sambrook J and Russell D W. in Molecular Cloning. 2001; page: 15.25-15.35, Cold Spring Harbor Laboratory Press, New York, US
115. Sambrook J and Russell D W. in Molecular Cloning. 2001; page: 15.51-15.52, Cold Spring Harbor Laboratory Press, New York, US 116. Sambrook J and Russell D W. in Molecular Cloning. 2001; page: 15.25-15.29 and 15-49-15-53, Cold Spring Harbor Laboratory Press, New York, US
117. Chou T C, et al. Reversal of anticancer multidrug resistance by the ardeemins. Proc Natl Acad Sci USA. 1998; 95(14): 8369-8374
118. Corbell T, et al. in vivo methods for screening and preclinical testing: use of rodent solid tumors for drug discovery, in Anticancer Drug Development Guide: preclinical screening, clinical trails, and approval. Edited by Teicher B A and Andrews P A. 2004; page: 79-124. Humana Press, New Jersey, US

What is claimed is:

1. A protein exhibiting human interferon-like anti-viral and anti-proliferative biological activities, wherein said protein is selected from the group consisting of proteins each comprising an amino acid sequence at least 89% identical to SEQ ID No: 2.

2. The protein as defined in claim 1, wherein said sequence is at least 90% identical to SEQ ID NO: 2.

3. The protein as defined in claim 1, wherein said sequence is at least 95% identical to SEQ ID NO: 2.

4. The protein as defined in claim 1, wherein said protein has enhanced anti-viral and anti-proliferative activity in comparison to HuIFN-α2b.

5. The protein as defined in claim 4, wherein said protein has anti-viral activity at least 2 fold greater than HuIFN-α2b.

6. The protein as defined in claim 5, wherein said protein has anti-viral activity at least 5 fold greater than HuIFN-α2b.

7. The protein as defined in claim 6, wherein said protein has anti-viral activity at least 10 fold greater than HuIFN-α2b.

8. The protein as defined in claim 4, wherein said protein has anti-proliferative activity at least 10 fold greater than HuIFN-α2b.

9. The protein as defined in claim 8, wherein said protein has anti-proliferative activity at least 50 fold greater than HuIFN-α2b.

10. The protein as defined in claim 9, wherein said protein has anti-proliferative activity at least 100 fold greater than HuIFN-α2b.

11. The protein as defined in claim 10, wherein said protein has anti-proliferative activity at least 200 fold greater than HuIFN-α2b.

12. The protein as defined in claim 1, wherein said protein is recombinantly produced.

13. The protein as defined in claim 1, wherein said protein has a molecular weight of approximately 19315 daltons.

14. The protein as defined in claim 1, optionally comprising a methionine residue at the N terminus.

15. A protein comprising a sequence which differs in 0 to 10 amino acids from SEQ ID NO: 2, wherein said protein exhibits human inter-feron-like anti-viral and anti-proliferative biological activities.

16. The protein as defined in claim 15, wherein said protein has enhanced anti-viral and anti-proliferative activity in comparison to HuIFN-α2b.

17. The protein as defined in claim 16, wherein said protein has anti-viral activity at least 2 fold greater than HuIFN-α2b.

18. The protein as defined in claim 16, wherein said protein has anti-proliferative activity at least 10 fold greater than HuIFN-α2b.

19. The protein as defined in claim 15, wherein said protein is an interferon analogue.

20. A protein construct comprising the protein as defined in claim 1 coupled to another moiety, wherein said construct exhibits said human interferon-like biological activities.

21. The protein construct as defined in claim 20, wherein said protein is glycosylated.

22. The protein construct as defined in claim 20, wherein said moiety is a polypeptide.

23. The protein construct as defined in claim 20, wherein said moiety is a non-polypeptide.

24. The protein construct as defined in claim 23, wherein said moiety is a polymer molecule.

25. The protein construct as defined in claim 24, wherein said polymer molecule is a linear or branched polyethylene glycol.

26. The protein construct as defined in claim 20, wherein said moiety is a labeling molecule.

27. A composition comprising the protein as defined in claim 1 and a pharmaceutically acceptable carrier, diluent or excipient.

28. A protein exhibiting human interferon-like biological activities, wherein said protein has an amino acid sequence at least 95% identical to SEQ. ID NO. 2 and wherein said protein has enhanced anti-viral and anti-proliferative activities in comparison to HuIFN-α2b.

29. A composition comprising the protein of claim 28.

30. A protein having the amino acid sequence of SEQ ID NO: 2.

31. A protein exhibiting anti-viral and anti-proliferative biological activities at least as active as human IFN α2b, wherein said protein is selected from the group consisting of proteins each comprising an amino acid sequence at least 89% identical to SEQ ID NO: 2.

32. The protein as defined in claim 31, wherein said sequence is at least 95% identical to SEQ ID NO: 2.

33. The protein as defined in claim 31, wherein said sequence is at least 99% identical to SEQ ID NO: 2.

34. The protein as defined in claim 31, wherein said protein exhibits enhanced in vitro and in vivo anti-viral and anti-proliferative biological activities in comparison to human IFN α2b.

* * * * *

SEQUENCE LISTING

<160> NUMBER OF SEQ ID NOS: 17

<210> SEQ ID NO 1
<211> LENGTH: 498
<212> TYPE: DNA
<213> ORGANISM: Artificial sequence
<220> FEATURE:
<223> OTHER INFORMATION: Chemically synthesized nucleotide sequence

<400> SEQUENCE: 1

```
tgtaatctgt ctcaaaccca cagcctgggt agcaagagga ccttgatgct cctggcgcag      60
atggggaaaa tctccctttt ctcctgcctg aaggacagac atgactttga atttccccag     120
gaggaatttg atggcaacca gttccagaaa gctcaagcca tctctgtcct ccatgagctg     180
atccagcaga ccttcaatct cttcagcaca aaggaatcat ctgctgcttg ggatgagggc     240
ctcctagaca aattccgcac cgaactctac cggcagctaa atgacttgga agcctgtatg     300
atgcaggagg ttggggtgga agagactccc ctgatgaatg cggactccat cctggctgtg     360
aagaaatact ccaaagaat cactctttat ctgatggaga gaaatacag cccttgtgcc      420 tgggaggttg tcagagtaga aatcatgaga tccctctctt tttcaacaaa cttgcaaaaa     480
agattaaggg ggaaggat                                                  498
```

<210> SEQ ID NO 2
<211> LENGTH: 166
<212> TYPE: PRT
<213> ORGANISM: Artificial Sequence
<220> FEATURE:
<223> OTHER INFORMATION: Chemically synthesized amino acid sequence

<400> SEQUENCE: 2

```
Cys Asn Leu Ser Gln Thr His Ser Leu Gly Ser Lys Arg Thr Leu Met
1               5                   10                  15

Leu Leu Ala Gln Met Gly Lys Ile Ser Leu Phe Ser Cys Leu Lys Asp
            20                  25                  30

Arg His Asp Phe Glu Phe Pro Gln Glu Glu Phe Asp Gly Asn Gln Phe
        35                  40                  45

Gln Lys Ala Gln Ala Ile Ser Val Leu His Glu Leu Ile Gln Gln Thr
    50                  55                  60

Phe Asn Leu Phe Ser Thr Lys Glu Ser Ser Ala Ala Trp Asp Glu Gly
65                  70                  75                  80

Leu Leu Asp Lys Phe Arg Thr Glu Leu Tyr Arg Gln Leu Asn Asp Leu
                85                  90                  95

Glu Ala Cys Met Met Gln Glu Val Gly Val Glu Glu Thr Pro Leu Met
            100                 105                 110

Asn Ala Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Val Glu Ile Met Arg Ser Leu Ser Phe Ser Thr Asn Leu Gln Lys
```

```
145                 150                 155                 160

Arg Leu Arg Gly Lys Asp
                165

<210> SEQ ID NO 3
<211> LENGTH: 19
<212> TYPE: DNA
<213> ORGANISM: Artificial sequence
<220> FEATURE:
<223> OTHER INFORMATION: Chemically synthesized nucleotide sequence

<400> SEQUENCE: 3
tggtgctcag ctrcaagtc                                              19

<210> SEQ ID NO 4
<211> LENGTH: 22
<212> TYPE: DNA
<213> ORGANISM: Artificial sequence
<220> FEATURE:
<223> OTHER INFORMATION: Chemically synthesized nucleotide sequence

<400> SEQUENCE: 4
aatcatttcc atgttgracc ag                                          22

<210> SEQ ID NO 5
<211> LENGTH: 22
<212> TYPE: DNA
<213> ORGANISM: Artificial sequence
<220> FEATURE:
<223> OTHER INFORMATION: Chemically synthesized nucleotide sequence

<400> SEQUENCE: 5
aatcatttcc cggttgtacc ag                                          22

<210> SEQ ID NO 6
<211> LENGTH: 22
<212> TYPE: DNA
<213> ORGANISM: Artificial sequence
<220> FEATURE:
<223> OTHER INFORMATION: Chemically synthesized nucleotide sequence

<400> SEQUENCE: 6
aatcatttcc atgttgaaac ag                                          22

<210> SEQ ID NO 7
<211> LENGTH: 22
<212> TYPE: DNA
<213> ORGANISM: Artificial sequence
<220> FEATURE:
<223> OTHER INFORMATION: Chemically synthesized nucleotide sequence

<400> SEQUENCE: 7
aatcatttca agatgagccc ag                                          22

<210> SEQ ID NO 8
<211> LENGTH: 22
<212> TYPE: DNA
<213> ORGANISM: Artificial sequence
<220> FEATURE:
<223> OTHER INFORMATION: Chemically synthesized nucleotide sequence

<400> SEQUENCE: 8
aatgattttc atgttgaacc ag                                          22

<210> SEQ ID NO 9
```

```
<211> LENGTH: 22
<212> TYPE: DNA
<213> ORGANISM: Artificial sequence
<220> FEATURE:
<223> OTHER INFORMATION: Chemically synthesized nucleotide sequence

<400> SEQUENCE: 9
aatcatttss atgttgaacc ag                                              22

<210> SEQ ID NO 10
<211> LENGTH: 22
<212> TYPE: DNA
<213> ORGANISM: Artificial sequence
<220> FEATURE:
<223> OTHER INFORMATION: Chemically synthesized nucleotide sequence

<400> SEQUENCE: 10
gatcatttcc atgttgaatg ag                                              22

<210> SEQ ID NO 11
<211> LENGTH: 23
<212> TYPE: DNA
<213> ORGANISM: Artificial sequence
<220> FEATURE:
<223> OTHER INFORMATION: Chemically synthesized nucleotide sequence

<400> SEQUENCE: 11
gagtcgtttc tgtgttggat cag                                             23

<210> SEQ ID NO 12
<211> LENGTH: 22
<212> TYPE: DNA
<213> ORGANISM: Artificial sequence
<220> FEATURE:
<223> OTHER INFORMATION: Chemically synthesized nucleotide sequence

<400> SEQUENCE: 12
atgcccctgt ccttttcttt ac                                              22

<210> SEQ ID NO 13
<211> LENGTH: 19
<212> TYPE: DNA
<213> ORGANISM: Artificial sequence
<220> FEATURE:
<223> OTHER INFORMATION: Chemically synthesized nucleotide sequence

<400> SEQUENCE: 13
agggcagcat tcaaagcag                                                  19

<210> SEQ ID NO 14
<211> LENGTH: 21
<212> TYPE: DNA
<213> ORGANISM: Artificial sequence
<220> FEATURE:
<223> OTHER INFORMATION: Chemically synthesized nucleotide sequence

<400> SEQUENCE: 14
tcagaccgct tctgcgttct g                                               21

<210> SEQ ID NO 15
<211> LENGTH: 19
<212> TYPE: DNA
<213> ORGANISM: Artificial sequence
<220> FEATURE:
<223> OTHER INFORMATION: Chemically synthesized nucleotide sequence

<400> SEQUENCE: 15
```

```
gaaggctttg gggtgtgtg                                                    19

<210> SEQ ID NO 16
<211> LENGTH: 17
<212> TYPE: DNA
<213> ORGANISM: Artificial sequence
<220> FEATURE:
<223> OTHER INFORMATION: Chemically synthesized nucleotide sequence

<400> SEQUENCE: 16
aatcttctct catccgc                                                      17

<210> SEQ ID NO 17
<211> LENGTH: 18
<212> TYPE: DNA
<213> ORGANISM: Artificial sequence
<220> FEATURE:
<223> OTHER INFORMATION: Chemically synthesized nucleotide sequence

<400> SEQUENCE: 17
accatgaagg                                                              18
```